US012590081B2

(12) United States Patent
Yang et al.

(10) Patent No.: US 12,590,081 B2
(45) Date of Patent: Mar. 31, 2026

(54) FUSED IMIDAZOLE DERIVATIVES, PREPARATION METHOD AND MEDICINAL USE THEREOF

(71) Applicant: Jiangsu Hengrui Pharmaceuticals Co., Ltd., Lianyungang (CN)

(72) Inventors: Fanglong Yang, Shanghai (CN); Qian Yang, Shanghai (CN); Feng He, Shanghai (CN); Weikang Tao, Shanghai (CN)

(73) Assignee: Jiangsu Hengrui Pharmaceuticals Co., Ltd., Lianyungang (CN)

( * ) Notice: Subject to any disclaimer, the term of this patent is extended or adjusted under 35 U.S.C. 154(b) by 719 days.

(21) Appl. No.: 17/907,458

(22) PCT Filed: Apr. 2, 2021

(86) PCT No.: PCT/CN2021/085229
§ 371 (c)(1),
(2) Date: Sep. 27, 2022

(87) PCT Pub. No.: WO2021/197464
PCT Pub. Date: Oct. 7, 2021

(65) Prior Publication Data

US 2023/0126875 A1 Apr. 27, 2023

(30) Foreign Application Priority Data

Apr. 3, 2020 (CN) ......................... 202010257986.6
Apr. 30, 2020 (CN) ......................... 202010362275.5
Jun. 19, 2020 (CN) ......................... 202010565231.2

(51) Int. Cl.
*C07D 401/14* (2006.01)
*A61K 31/4439* (2006.01)
*A61K 31/444* (2006.01)
*A61P 3/10* (2006.01)
*C07D 405/14* (2006.01)
*C07D 471/04* (2006.01)

(52) U.S. Cl.
CPC ......... *C07D 405/14* (2013.01); *C07D 471/04* (2013.01)

(58) Field of Classification Search
CPC .. C07D 401/14; C07D 405/14; C07D 471/04; A61K 31/444; A61K 31/4439; A61P 3/10
See application file for complete search history.

(56) References Cited

U.S. PATENT DOCUMENTS 10,844,049 B2 * 11/2020 Zhong ....................... A61P 1/16
10,858,356 B2 12/2020 Yoshino et al.
10,954,221 B2 * 3/2021 Zhong .................. C07D 471/04
11,591,321 B2 * 2/2023 Zhong .................. C07D 471/04
12,227,499 B2 2/2025 Yang et al.
12,365,670 B2 * 7/2025 Zhong .................. C07D 498/04
2023/0165846 A1 * 6/2023 Meng ......................... A61P 3/10 514/255.05
2023/0322756 A1 10/2023 Jiangsu
2024/0246958 A1 7/2024 Jiangsu
2025/0042883 A1 * 2/2025 Zhong .................. C07D 417/14
2025/0243195 A1 7/2025 Yang et al.

FOREIGN PATENT DOCUMENTS

| | | | |
|---|---|---|---|
| CN | 110325530 | A | 10/2019 |
| JP | 656778 | B2 | 8/2019 |
| WO | WO-2007/060409 | A1 | 5/2007 |
| WO | 2009111700 | A2 | 9/2009 |
| WO | 2010114824 | A1 | 10/2010 |
| WO | 2018109607 | A1 | 6/2018 |
| WO | 2019239319 | A1 | 12/2019 |
| WO | 2019239371 | A1 | 12/2019 |
| WO | 2020103815 | A1 | 5/2020 |
| WO | 2020207474 | A1 | 10/2020 |
| WO | 2021018023 | A1 | 2/2021 |
| WO | WO-2021/160127 | A1 | 8/2021 |

OTHER PUBLICATIONS

International Search Report issued Jun. 24, 2021 in PCT/CN2021/085229.
U.S. Appl. No. 19/012,024, filed Jan. 7, 2025, Yang et al.

* cited by examiner

*Primary Examiner* — Brenda L Coleman
(74) *Attorney, Agent, or Firm* — Choate, Hall & Stewart LLP; Michael A. Shinall; Erica M. D'Amato

(57) ABSTRACT

The present disclosure relates to fused imidazole derivatives, preparation methods and medical use thereof. Specifically, the present disclosure relates to a fused imidazole derivative represented by the general formula (I), the preparation method thereof, and the pharmaceutical composition containing the same, as well as the use as a therapeutic agent, especially as GLP-1 receptor agonists, and the use thereof in the preparation of medicaments for the treatment and/or prevention of diabetes. The substituents of general formula (I) are the same as defined in the specification.

(I)

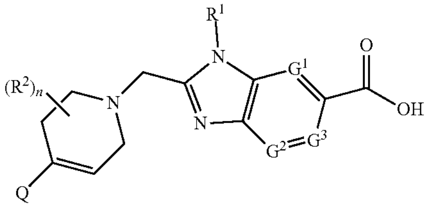

21 Claims, No Drawings

FUSED IMIDAZOLE DERIVATIVES, PREPARATION METHOD AND MEDICINAL USE THEREOF

CROSS-REFERENCE TO RELATED APPLICATION

This application is a Section 371 of International Application No. PCT/CN2021/085229 filed Apr. 2, 2021, which was published in the Chinese language Oct. 7, 2021, under International Publication No. WO 2021/197464 A1, which claims priority to Chinese Patent Application No. 202010257986.6 filed Apr. 3, 2020; Chinese Patent Application No. 202010362275.5 filed Apr. 30, 2020; and Chinese Patent Application No. 202010565231.2 filed Jun. 19, 2020, the disclosures of which are incorporated herein by reference in their entireties.

TECHNICAL FIELD

The present disclosure belongs to the field of pharmaceutics, and relates to a fused imidazole derivative, a preparation method therefor and pharmaceutical use thereof. In particular, the present disclosure relates to a fused imidazole derivative of general formula (I), a preparation method therefor, a pharmaceutical composition comprising the derivative, and use of the derivative as a GLP-1 receptor agonist in the field of diabetes treatment.

BACKGROUND

Diabetes is a metabolic disease of multiple etiologies characterized by chronic hyperglycemia accompanied with disturbances in the metabolism of sugars, lipids and proteins due to a deficiency of insulin secretion or its action. Diabetes is a very ancient disease, and is caused by the absolute or relative deficiency of insulin in a human body, so that the concentration of glucose in blood is increased, and then a large amount of sugar is discharged from urine, accompanied with symptoms such as polydipsia, diuresis, polyphagia and emaciation.

Generally, there are two types of diabetes. Patients with type I diabetes, i.e., patients with insulin-dependent diabetes, produce little or no insulin by themselves. Insulin is a hormone used in the body to regulate glucose utilization. Patients with type II diabetes, i.e., patients with non-insulin-dependent diabetes, have the same or higher insulin level in their plasma as or than the non-diabetic population. However, such patients develop resistance to insulin which stimulates glucose and lipid metabolism in cells of major insulin-sensitive tissues, such as muscle, liver and adipose tissue. Even with elevated plasma insulin level, the patients' significant resistance to insulin cannot be overcome.

In addition to insulin resistance resulting from a reduction in the number of insulin receptors, a deficiency of insulin receptors can also lead to insulin resistance and this mechanism has not been fully understood. Insulin responsiveness (insulin resistance) results in failure of insulin to activate the uptake, oxidation and storage of glucose in muscle tissue, failure of effective inhibition of lipolysis in adipose tissue, and failure of regulation of the production and secretion of glucose in the liver.

Glucagon-like peptide-1 (GLP-1) is an incretin hormone secreted from L-cells in the distal intestine.

GLP-1 plays a corresponding role by binding to its ubiquitous specific receptor. Organs in which GLP-1 receptor is now clearly present include islet cells, gastrointestinal, pulmonary, brain, kidney, hypothalamus and cardiovascular systems, and GLP-1 receptor may also be present in liver, adipose tissue and skeletal muscle. GLP-1 not only acts on β cells to promote insulin secretion, but also acts on a cells to inhibit glucagon secretion. There is generally no significant difference in serum GLP-1 levels in patients with normal glucose tolerance, impaired glucose tolerance, and type II diabetes. However, there is a deficiency of the response of β cells to GLP-1 after eating, and under certain conditions, the response is significantly enhanced after continuous infusion of GLP-1. Since the duration of action of human GLP-1 is very short ($t_{1/2}<1.5$ minutes via intravenous injection), human GLP-1 is not suitable for clinical treatment of diabetes.

Peptidic GLP-1 receptor agonists (e.g., liraglutide and exenatide) have effects on improving blood glucose level in type II diabetic patients by lowering fasting and postprandial glucose. However, since the peptidic GLP-1 has poor oral bioavailability and is inconvenient to take, small molecule agonists of GLP-1 receptors with good oral bioavailability are highly desirable.

The small molecule agonists of GLP-1 receptors are disclosed in patent applications including WO2009111700, WO2010114824, WO2018109607, WO2019239319, WO2018056453, and the like.

SUMMARY

The present disclosure is intended to provide a compound of general formula (I) or a tautomer, mesomer, racemate, enantiomer or diastereomer thereof or a mixture thereof, or a pharmaceutically acceptable salt thereof:

(I)

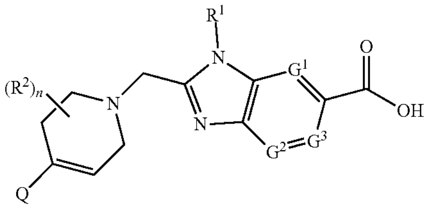

wherein:

Q is Q0 or Q2,

Q0

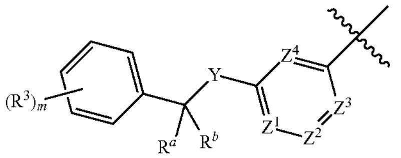

or

Q2

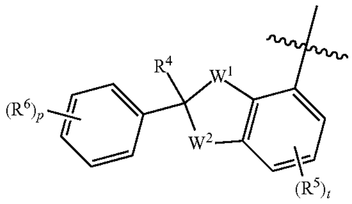

;

$G^1$, $G^2$ and $G^3$ are identical or different and are each independently $CR^7$ or an N atom;

$Z^1$, $Z^2$, $Z^3$ and $Z^4$ are identical or different and are each independently $CR^8$ or an N atom;

Y is selected from the group consisting of an O atom, an S atom, $NR^9$ and $CR^{10}R^{11}$;

$W^1$ and $W^2$ are identical or different and are each independently selected from the group consisting of an O atom, an S atom, $NR^{12}$ and $CR^{13}R^{14}$;

$R^a$ and $R^b$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^1$ is selected from the group consisting of a hydrogen atom, alkyl, alkenyl, alkynyl, haloalkyl, hydroxyalkyl, cycloalkyl, heterocyclyl, aryl and heteroaryl, wherein the alkyl, alkenyl, alkynyl, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^2$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, alkoxy, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^3$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, alkoxy, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^4$ is selected from the group consisting of a hydrogen atom, halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^5$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, alkoxy, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^6$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, alkoxy, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^7$ and $R^8$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

$R^9$ and $R^{12}$ are identical or different and are each independently selected from the group consisting of a hydrogen atom, alkyl, alkenyl, alkynyl, haloalkyl, hydroxyalkyl, amino, hydroxy, cycloalkyl, heterocyclyl, aryl and heteroaryl;

$R^{10}$, $R^{11}$, $R^{13}$ and $R^{14}$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

n is 0, 1, 2, 3, 4 or 5;

m is 0, 1, 2, 3, 4 or 5;

t is 0, 1, 2 or 3; and p is 0, 1, 2, 3, 4 or 5.

The present disclosure is intended to provide a compound of general formula (I) or a tautomer, mesomer, racemate, enantiomer or diastereomer thereof or a mixture thereof, or a pharmaceutically acceptable salt thereof:

(I)

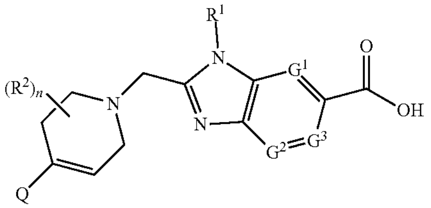

wherein:

Q is Q1 or Q2,

Q1

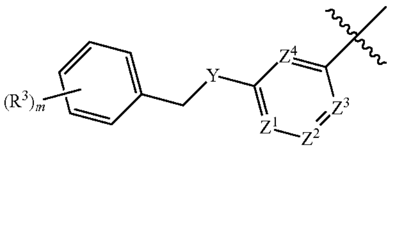

or

-continued

Q2

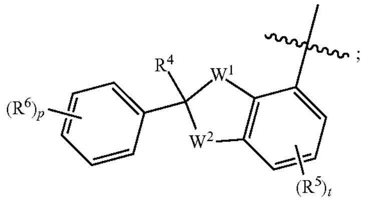

$G^1$, $G^2$ and $G^3$ are identical or different and are each independently $CR^7$ or an N atom;

$Z^1$, $Z^2$, $Z^3$ and $Z^4$ are identical or different and are each independently $CR^8$ or an N atom;

Y is selected from the group consisting of an O atom, an S atom, $NR^9$ and $CR^{10}R^{11}$;

$W^1$ and $W^2$ are identical or different and are each independently selected from the group consisting of an O atom, an S atom, $NR^{12}$ and $CR^{13}R^{14}$;

$R^1$ is selected from the group consisting of a hydrogen atom, alkyl, alkenyl, alkynyl, haloalkyl, hydroxyalkyl, cycloalkyl, heterocyclyl, aryl and heteroaryl, wherein the alkyl, alkenyl, alkynyl, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^2$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, alkoxy, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^3$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, alkoxy, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^4$ is selected from the group consisting of a hydrogen atom, halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^5$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, alkoxy, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^6$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, alkoxy, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^7$ and $R^8$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

$R^9$ and $R^{12}$ are identical or different and are each independently selected from the group consisting of a hydrogen atom, alkyl, alkenyl, alkynyl, haloalkyl, hydroxyalkyl, amino, hydroxy, cycloalkyl, heterocyclyl, aryl and heteroaryl;

$R^{10}$, $R^{11}$, $R^{13}$ and $R^{14}$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

n is 0, 1, 2, 3, 4 or 5;

m is 0, 1, 2, 3, 4 or 5;

t is 0, 1, 2 or 3; and p is 0, 1, 2, 3, 4 or 5.

In some preferred embodiments of the present disclosure, provided is the compound of general formula (I) or the tautomer, mesomer, racemate, enantiomer or diastereomer thereof or the mixture thereof, or the pharmaceutically acceptable salt thereof, wherein $G^1$ is CH or an N atom; $G^2$ and $G^3$ are both CH; preferably, $G^1$, $G^2$ and $G^3$ are all CH.

In some preferred embodiments of the present disclosure, provided is the compound of general formula (I) or the tautomer, mesomer, racemate, enantiomer or diastereomer thereof or the mixture thereof, or the pharmaceutically acceptable salt thereof, which is a compound of general formula (II) or a tautomer, mesomer, racemate, enantiomer or diastereomer thereof or a mixture thereof, or a pharmaceutically acceptable salt thereof:

(II)

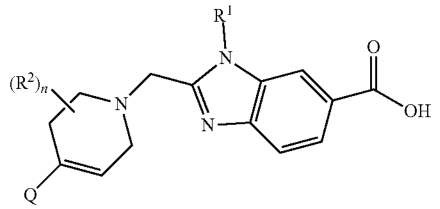

wherein:

$R^1$, $R^2$, Q and n are as defined in general formula (I).

In some preferred embodiments of the present disclosure, provided is the compound of general formula (I) or general formula (II) or the tautomer, mesomer, racemate, enantiomer or diastereomer thereof or the mixture thereof, or the pharmaceutically acceptable salt thereof, wherein $Z^1$, $Z^2$ and $Z^3$ are identical or different and are each independently $CR^8$, and $Z^4$ is an N atom; $R^8$ is a hydrogen atom or halogen.

In some preferred embodiments of the present disclosure, provided is the compound of general formula (I) or general formula (II) or the tautomer, mesomer, racemate, enantiomer or diastereomer thereof or the mixture thereof, or the pharmaceutically acceptable salt thereof, wherein Y is an O atom or an S atom.

In some preferred embodiments of the present disclosure, provided is the compound of general formula (I) or general formula (II) or the tautomer, mesomer, racemate, enantiomer or diastereomer thereof or the mixture thereof, or the pharmaceutically acceptable salt thereof, wherein $Z^1$, $Z^2$ and $Z^3$ are all CH, and $Z^4$ is an N atom; and/or Y is an O atom.

In some preferred embodiments of the present disclosure, provided is the compound of general formula (I) or general formula (II) or the tautomer, mesomer, racemate, enantiomer or diastereomer thereof or the mixture thereof, or the pharmaceutically acceptable salt thereof, wherein $W^1$ and $W^2$ are both O atoms.

In some embodiments of the present disclosure, provided is the compound of general formula (I) or general formula (II) or the tautomer, mesomer, racemate, enantiomer or diastereomer thereof or the mixture thereof, or the pharmaceutically acceptable salt thereof, wherein Q is selected from the group consisting of Q3, Q4, Q5 and Q6:

Q3

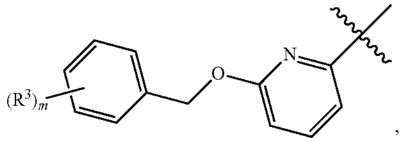

,

Q4

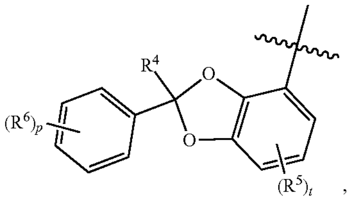

,

Q5

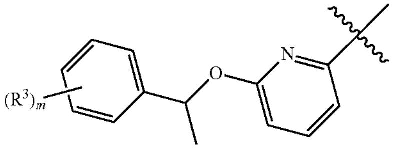

and

Q6

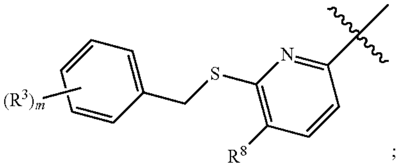

;

$R^3$-$R^6$, $R^8$, m, p and t are as defined in general formula (I).

In some embodiments of the present disclosure, provided is the compound of general formula (I) or general formula (II) or the tautomer, mesomer, racemate, enantiomer or diastereomer thereof or the mixture thereof, or the pharmaceutically acceptable salt thereof, wherein Q is selected from the group consisting of Q3, Q4 and Q5:

Q3

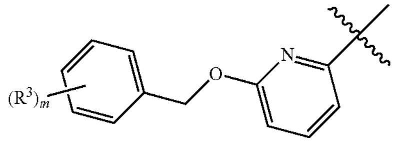

Q4

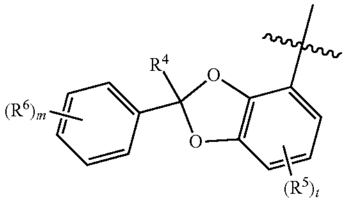

or

Q5

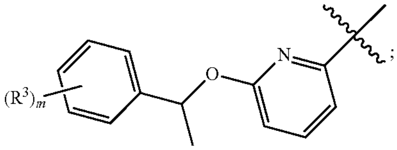

;

$R^3$-$R^6$, m, p and t are as defined in general formula (I).

In some embodiments of the present disclosure, provided is the compound of general formula (I) or general formula (II) or the tautomer, mesomer, racemate, enantiomer or diastereomer thereof or the mixture thereof, or the pharmaceutically acceptable salt thereof, wherein Q is

Q4

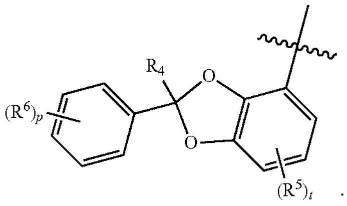

.

In some embodiments of the present disclosure, provided is the compound of general formula (I) or general formula (II) or the tautomer, mesomer, racemate, enantiomer or diastereomer thereof or the mixture thereof, or the pharmaceutically acceptable salt thereof, which is a compound of general formula (III) or a tautomer, mesomer, racemate, enantiomer or diastereomer thereof or a mixture thereof, or a pharmaceutically acceptable salt thereof:

(III)

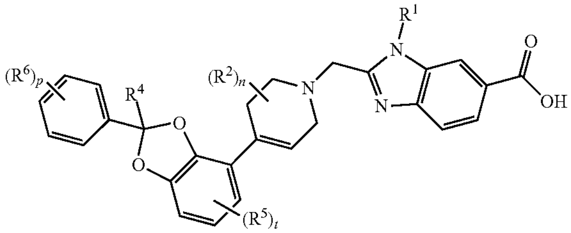

$R^1$, $R^2$, $R^4$-$R^6$, n, p and t are as defined in general formula (I).

In some embodiments of the present disclosure, provided is the compound of general formula (I), general formula (II)

or general formula (III) or the tautomer, mesomer, racemate, enantiomer or diastereomer thereof or the mixture thereof, or the pharmaceutically acceptable salt thereof, which is a compound of general formula (IIIaa) or a tautomer, mesomer, racemate, enantiomer or diastereomer thereof or a mixture thereof, or a pharmaceutically acceptable salt thereof:

(IIIaaa)

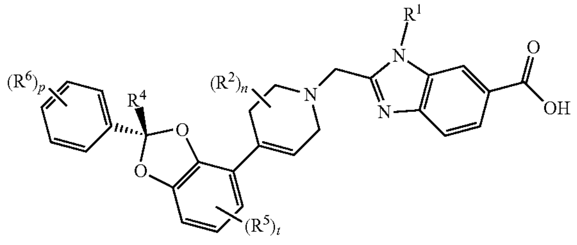

$R^1$, $R^2$, $R^4$-$R^6$, n, p and t are as defined in general formula (I).

In some embodiments of the present disclosure, provided is the compound of general formula (I), general formula (II), general formula (III) or general formula (IIIaa) or the tautomer, mesomer, racemate, enantiomer or diastereomer thereof or the mixture thereof, or the pharmaceutically acceptable salt thereof, wherein $R^1$ is $C_{1-6}$ alkyl, wherein the $C_{1-6}$ alkyl is optionally substituted with one or more substituents selected from the group consisting of halogen, hydroxy, $C_{1-6}$ alkoxy, 3- to 6-membered cycloalkyl and 3- to 6-membered heterocyclyl; preferably, $R^1$ is $C_{1-6}$ alkyl, wherein the $C_{1-6}$ alkyl is optionally substituted with one 3- to 6-membered heterocyclyl; more preferably, $R^1$ is

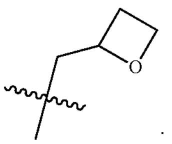 [SMILES: *CC1CCO1]

In some embodiments of the present disclosure, provided is the compound of general formula (I), general formula (II), general formula (III) or general formula (IIIaa) or the tautomer, mesomer, racemate, enantiomer or diastereomer thereof or the mixture thereof, or the pharmaceutically acceptable salt thereof, wherein $R^2$ are identical or different and are each independently a hydrogen atom or $C_{1-6}$ alkyl.

In some embodiments of the present disclosure, provided is the compound of general formula (I) or general formula (II) or the tautomer, mesomer, racemate, enantiomer or diastereomer thereof or the mixture thereof, or the pharmaceutically acceptable salt thereof, wherein $R^3$ are identical or different and are each independently selected from the group consisting of a hydrogen atom, halogen, $C_{1-6}$ alkyl and cyano.

In some embodiments of the present disclosure, provided is the compound of general formula (I), general formula (II), general formula (III) or general formula (IIIaa) or the tautomer, mesomer, racemate, enantiomer or diastereomer thereof or the mixture thereof, or the pharmaceutically acceptable salt thereof, wherein $R^4$ is a hydrogen atom or $C_{1-6}$ alkyl, and preferably $C_{1-6}$ alkyl.

In some embodiments of the present disclosure, provided is the compound of general formula (I), general formula (II), general formula (III) or general formula (IIIaa) or the tautomer, mesomer, racemate, enantiomer or diastereomer thereof or the mixture thereof, or the pharmaceutically acceptable salt thereof, wherein $R^5$ are identical or different and are each independently selected from the group consisting of a hydrogen atom, halogen and $C_{1-6}$ alkyl; and/or $R^6$ are identical or different and are each independently selected from the group consisting of a hydrogen atom, halogen and $C_{1-6}$ alkyl.

In some embodiments of the present disclosure, provided is the compound of general formula (I), general formula (II), general formula (III) or general formula (IIIaa) or the tautomer, mesomer, racemate, enantiomer or diastereomer thereof or the mixture thereof, or the pharmaceutically acceptable salt thereof, wherein n is 0 or 1.

In some embodiments of the present disclosure, provided is the compound of general formula (I), general formula (II), general formula (III) or general formula (IIIaa) or the tautomer, mesomer, racemate, enantiomer or diastereomer thereof or the mixture thereof, or the pharmaceutically acceptable salt thereof, wherein t is 0 or 1.

In some embodiments of the present disclosure, provided is the compound of general formula (I), general formula (II), general formula (III) or general formula (IIIaa) or the tautomer, mesomer, racemate, enantiomer or diastereomer thereof or the mixture thereof, or the pharmaceutically acceptable salt thereof, wherein p is 0, 1 or 2, and preferably 2.

In some embodiments of the present disclosure, provided is the compound of general formula (I) or the tautomer, mesomer, racemate, enantiomer or diastereomer thereof or the mixture thereof, or the pharmaceutically acceptable salt thereof, wherein $G^1$ is CH or an N atom; $G^2$ and $G^3$ are both CH; Q is

Q4

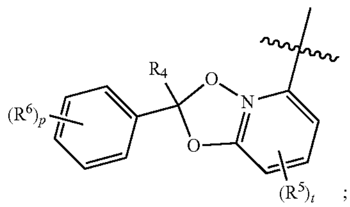

;

$R^1$ is

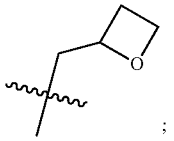 [SMILES: *CC1CCO1]

;

$R^2$ are identical or different and are each independently hydrogen or $C_{1-6}$ alkyl; $R^4$ is a hydrogen atom or $C_{1-6}$ alkyl; $R^5$ are identical or different and are each independently selected from the group consisting of a hydrogen atom, halogen and $C_{1-6}$ alkyl; $R^6$ are identical or different and are each independently selected from the group consisting of a hydrogen atom, halogen and $C_{1-6}$ alkyl; n is 0 or 1; t is 0 or 1; and p is 0, 1 or 2.

In some embodiments of the present disclosure, provided is the compound of general formula (II) or the tautomer, mesomer, racemate, enantiomer or diastereomer thereof or the mixture thereof, or the pharmaceutically acceptable salt thereof, wherein Q is

Q4

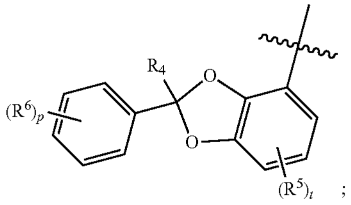

;

$R^1$ is

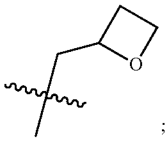 [SMILES: *CC1CCO1]

;

are identical or different and are each independently a hydrogen atom or $C_{1-6}$ alkyl; $R^4$ is a hydrogen atom or $C_{1-6}$ alkyl; $R^5$ are identical or different and are each independently selected from the group consisting of a hydrogen atom, halogen and $C_{1-6}$ alkyl; $R^6$ are identical or different and are each independently selected from the group consisting of a hydrogen atom, halogen and $C_{1-6}$ alkyl; n is 0 or 1; t is 0 or 1; and p is 0, 1 or 2.

TABLE A

Typical compounds disclosed herein include, but are not limited to:

| Example No. | Structure and name of compound |
|---|---|
| 1 | 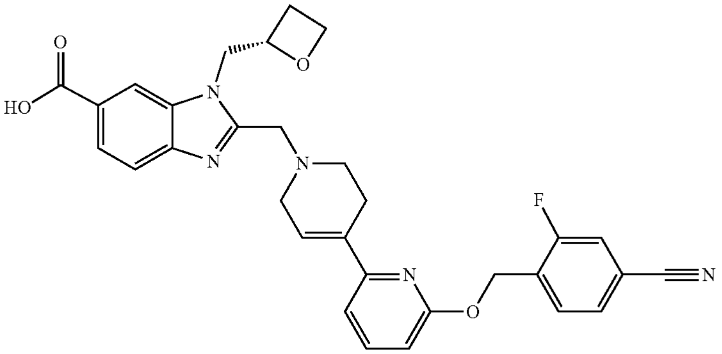 [SMILES: N#Cc1ccc(COc2cccc(C3=CCN(Cc4nc5ccc(C(=O)O)cc5n4C[C@@H]4CCO4)CC3)n2)c(F)c1]<br>1<br>(S)-2-((6-((4-cyano-2-fluorobenzyl)oxy-3',6'-dihydro-[2,4'-bipyridin]-1'(2'H)-yl)methyl)-1-(oxetan-2-ylmethyl)-1H-benzo[d]imidazole-6-carboxylic acid<br>1 |
| 2- | 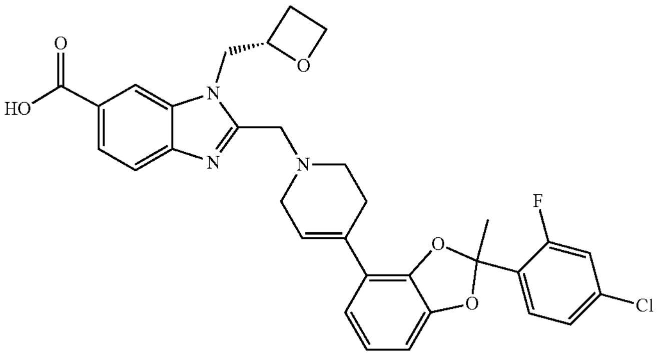 [SMILES: CC1(c2ccc(Cl)cc2F)Oc2cccc(C3=CCN(Cc4nc5ccc(C(=O)O)cc5n4C[C@@H]4CCO4)CC3)c2O1]<br>2<br>2-((4-(2-(4-chloro-2-fluorophenyl)-2-methylbenzo[d][1,3]dioxol-4-yl)-3,6-dihydropyridin-1(2H)-yl)methyl)-1-(((S)-oxetan-2-yl)methyl)-1H-benzo[d]imidazole-6-carboxylic acid 2 |

TABLE A-continued

| Typical compounds disclosed herein include, but are not limited to: |
| --- |

| Example No. | Structure and name of compound |
| --- | --- |
| 3 | 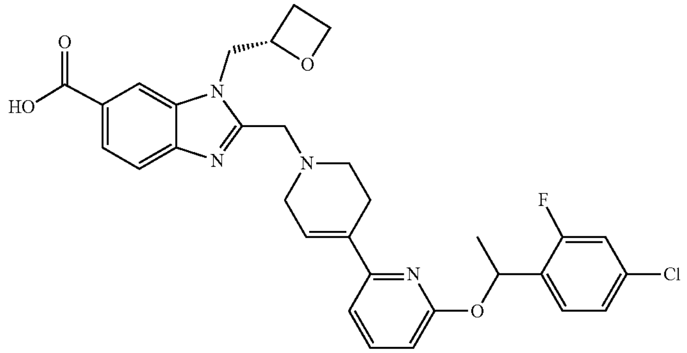 [SMILES: CC(Oc1cccc(C2=CCN(Cc3nc4ccc(C(=O)O)cc4n3C[C@@H]3CCO3)CC2)n1)c1ccc(Cl)cc1F] 3 2-((6-(1-(4-chloro-2-fluorophenyl)ethoxy)-3',6'-dihydro-[2,4'-bipyridin]-1'(2'H)-yl)methyl)-1-((S)-oxetan-2-yl)methyl)-1H-benzo[d]imidazole-6-carboxylic acid 3 |
| 4 | 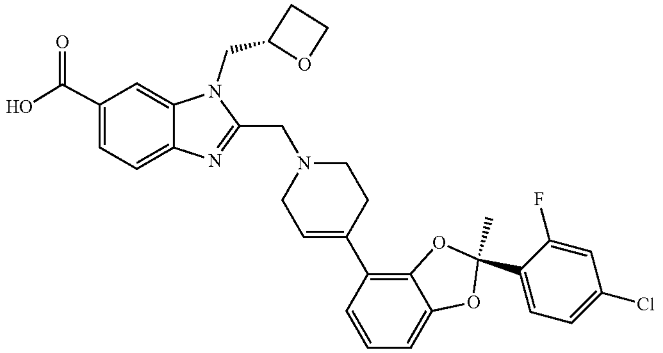 [SMILES: C[C@]1(c2ccc(Cl)cc2F)Oc2cccc(C3=CCN(Cc4nc5ccc(C(=O)O)cc5n4C[C@@H]4CCO4)CC3)c2O1] 4 2-((4-((S)-2-(4-chloro-2-fluorophenyl)-2-methylbenzo[d][1,3]dioxol-4-yl)-3,6-dihydropyridin-1(2H)-yl)methyl)-1-(((S)-oxetan-2-yl)methyl)-1H-benzo[d]imidazole-6-carboxylic acid 4 |
| 5 | 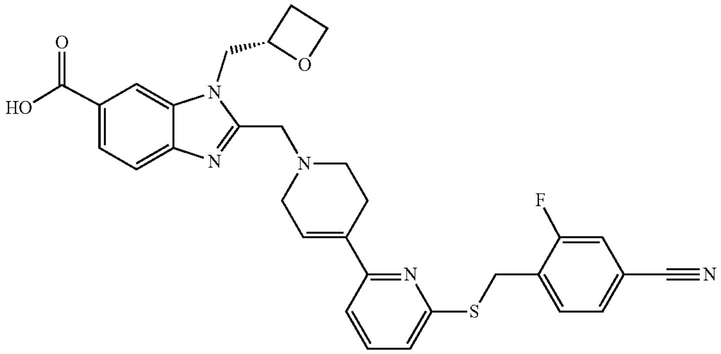 5 (S)-2-((6-(4-cyano-2-fluorobenzyl)thio-3',6'-dihydro-[2,4'-bipyridin]-1'(2'H)-yl)methyl)-1-(oxetan-2-ylmethyl)-1H-benzo[d]imidazole-6-carboxylic acid 5 |

TABLE A-continued

| Typical compounds disclosed herein include, but are not limited to: | |
|---|---|
| Example No. | Structure and name of compound |
| 6 | 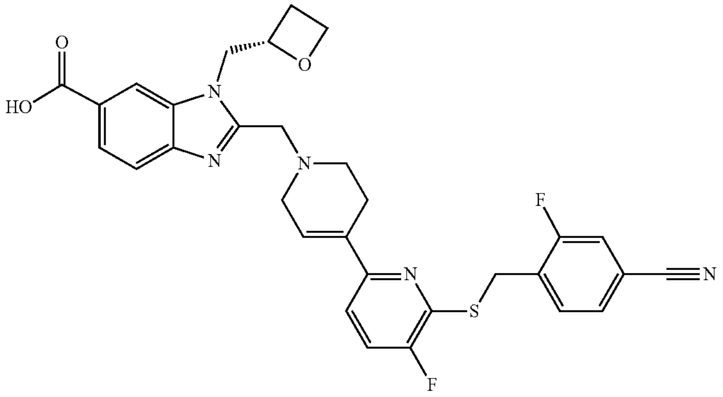 [SMILES: N#Cc1ccc(CSc2nc(C3=CCN(Cc4nc5ccc(C(=O)O)cc5n4C[C@@H]4CCO4)CC3)ccc2F)c(F)c1] 6 (S)-2-((6-(4-cyano-2-fluorobenzyl)thio-5-fluoro-3',6'-dihydro-[2,4'-bipyridin]-1'(2'H)-yl)methyl)-1-(oxetan-2-ylmethyl)-1H-benzo[d]imidazole-6-carboxylic acid 6 |
| 7 | 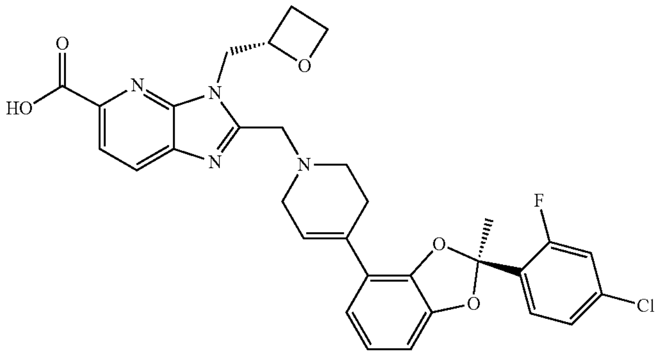 [SMILES: C[C@]1(c2ccc(Cl)cc2F)Oc2cccc(C3=CCN(Cc4nc5ccc(C(=O)O)nc5n4C[C@@H]4CCO4)CC3)c2O1] 7 2-((4-((S)-2-(4-chloro-2-fluorophenyl)-2-methylbenzo[d][1,3]dioxol-4-yl)-3,6-dihydropyridin-1(2H)-yl)methyl)-3-(((S)-oxetan-2-yl)methyl)-3H-imidazo[4,5-b]pyridine-5-carboxylic acid 7 |

Another aspect of the present disclosure relates to a compound of general formula (IA) or a tautomer, mesomer, racemate, enantiomer or diastereomer thereof or a mixture thereof, or a pharmaceutically acceptable salt thereof, (IA)

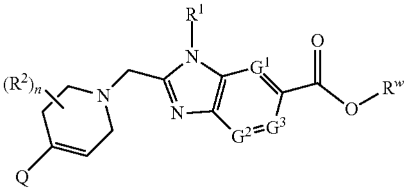

wherein:

$R^w$ is $C_{1-6}$ alkyl;

$G^1$, $G^2$, $G^3$, $R^1$, $R^2$, Q and n are as defined in general formula (I).

Another aspect of the present disclosure relates to a compound of general formula (IIA) or a tautomer, mesomer, racemate, enantiomer or diastereomer thereof or a mixture thereof, or a pharmaceutically acceptable salt thereof, (IIA)

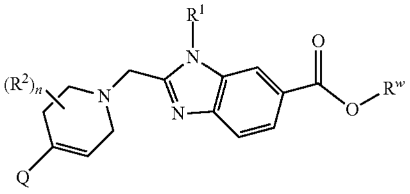

wherein:

$R^w$ is $C_{1-6}$ alkyl;

$R^1$, $R^2$, Q and n are as defined in general formula (II).

Another aspect of the present disclosure relates to a compound of general formula (IIIA) or a tautomer, mesomer, racemate, enantiomer or diastereomer thereof or a mixture thereof, or a pharmaceutically acceptable salt thereof, (IIIA)

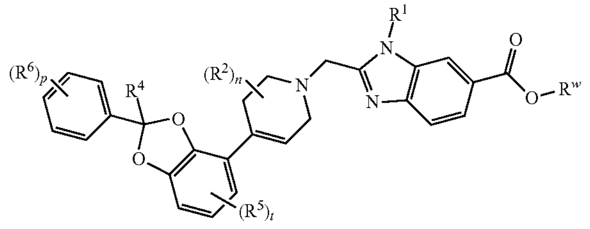

wherein:

$R^w$ is $C_{1-6}$ alkyl;

$R^1$, $R^2$, $R^4$-$R^6$, n, p and t are as defined in general formula (III).

Another aspect of the present disclosure relates to a compound of general formula (IIIaaA) or a tautomer, mesomer, racemate, enantiomer or diastereomer thereof or a mixture thereof, or a pharmaceutically acceptable salt thereof, (IIIaaA)

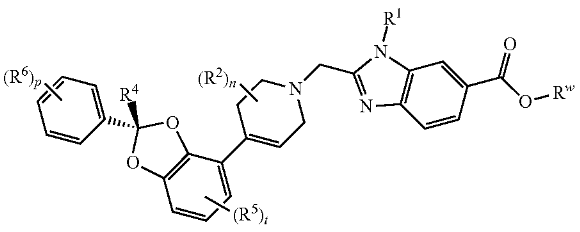

wherein:

$R^w$ is $C_{1-6}$ alkyl;

$R^1$, $R^2$, $R^4$-$R^6$, n, p and t are as defined in general formula (IIIaa).

Typical intermediate compounds disclosed herein include, but are not limited to:

| Example No. | Structure and name of compound |
| --- | --- |
| 1d | 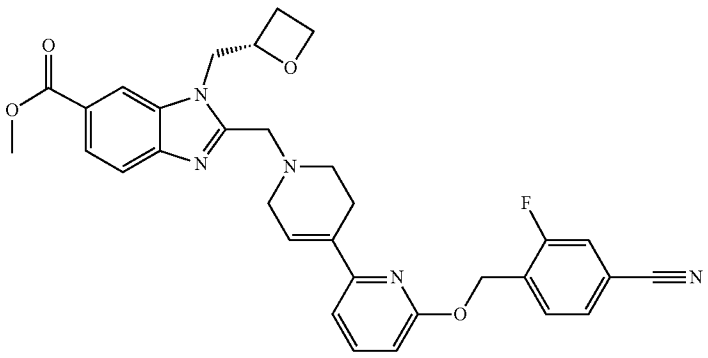 [SMILES: COC(=O)c1ccc2nc(CN3CC=C(c4cccc(OCc5ccc(C#N)cc5F)n4)CC3)n(C[C@@H]3CCO3)c2c1]<br>1d<br>Methyl (S)-2-((6-((4-cyano-2-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylate 1d |
| 2c | 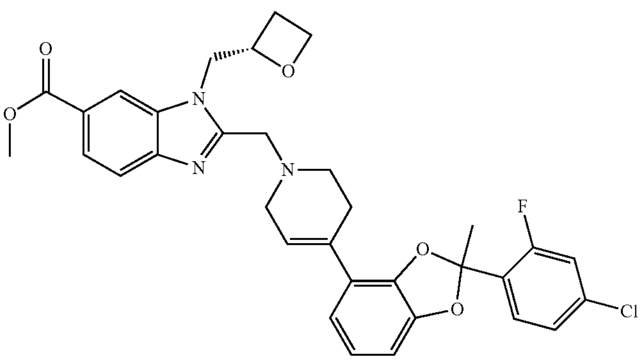 [SMILES: COC(=O)c1ccc2nc(CN3CC=C(c4cccc5c4OC(C)(c4ccc(Cl)cc4F)O5)CC3)n(C[C@@H]3CCO3)c2c1]<br>2c<br>Methyl 2-((4-(2-(4-chloro-2-fluorophenyl)-2-methylbenzo[d][1,3]dioxol-4-yl)-3,6-dihydropyridin-1(2H)-yl)methyl)-1-(((S)-oxetan-2-yl)methyl)-1H-benzo[d]imidazole-6-carboxylate 2c |

-continued

| Example No. | Structure and name of compound |
|---|---|
| 3g | 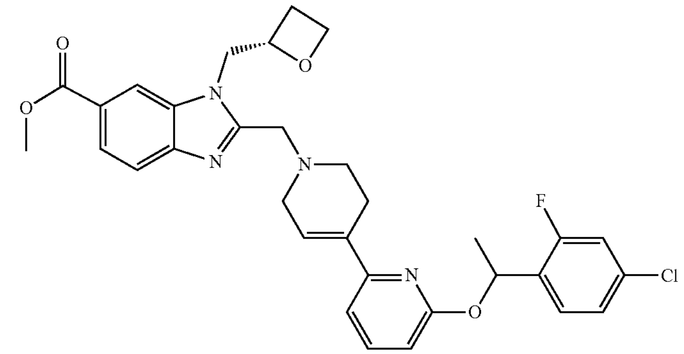 [SMILES: COC(=O)c1ccc2nc(CN3CC=C(c4cccc(OC(C)c5ccc(Cl)cc5F)n4)CC3)n(C[C@@H]3CCO3)c2c1]<br>3g<br>Methyl<br>2-((6-((4-chloro-2-fluorophenyl)ethoxy)-3',6'-dihydro-[2,4'-bipyridin]-1'(2'H)-yl)methyl)-1-((S)-oxetan-2-ylmethyl)-1H-benzo[d]imidazole-6-carboxylate<br>3g |
| 4c | 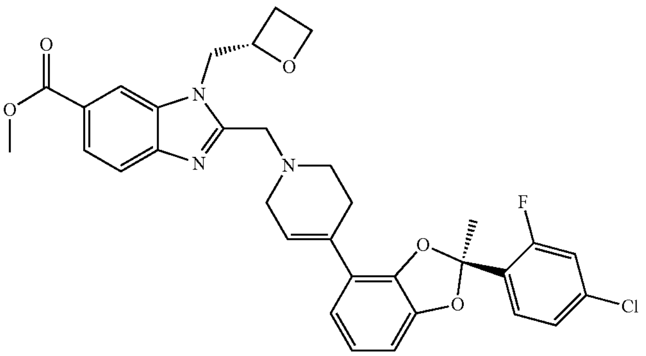 [SMILES: COC(=O)c1ccc2nc(CN3CC=C(c4cccc5c4O[C@@](C)(c4ccc(Cl)cc4F)O5)CC3)n(C[C@@H]3CCO3)c2c1]<br>4c<br>Methyl<br>2-((4-((S)-2-(4-chloro-2-fluorophenyl)-2-methylbenzo[d][1,3]dioxol-4-yl)-3,6-dihydropyridin-1(2H)-yl)methyl)-1-(((S)-oxetan-2-yl)methyl)-1H-benzo[d]imidazole-6-carboxylate 4c |
| 5e | 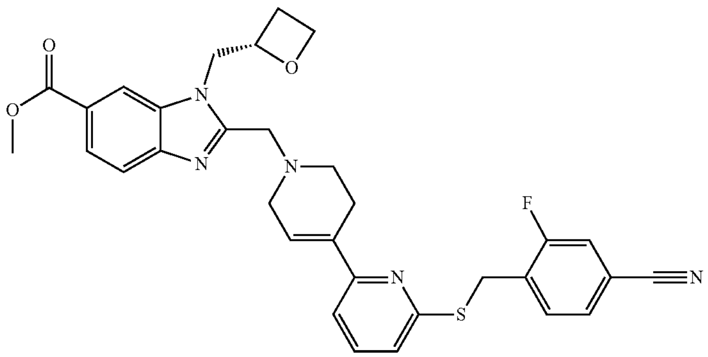<br>5e<br>Methyl<br>(S)-2-((6-((4-cyano-2-fluorobenzyl)thio)-3',6'-dihydro-[2,4'-bipyridin]-1'(2'H)-yl)methyl)-1-(oxetan-2-ylmethyl)-1H-benzo[d]imidazole-6-carboxylate 5e |

-continued

| Example No. | Structure and name of compound |
| --- | --- |
| 6d | 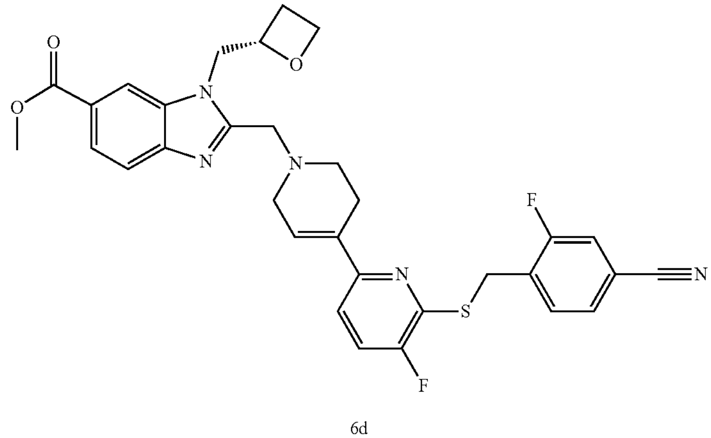<br>6d<br>Methyl<br>(S)-2-((6-((4-cyano-2-fluorobenzyl)thio)-5-fluoro-3',6'-dihydro-[2,4'-bipyridin]-1'(2'H)-yl)methyl)-1-(oxetan-2-ylmethyl)-1H-benzo[d]imidazole-6-carboxylate 6d |
| 7b | 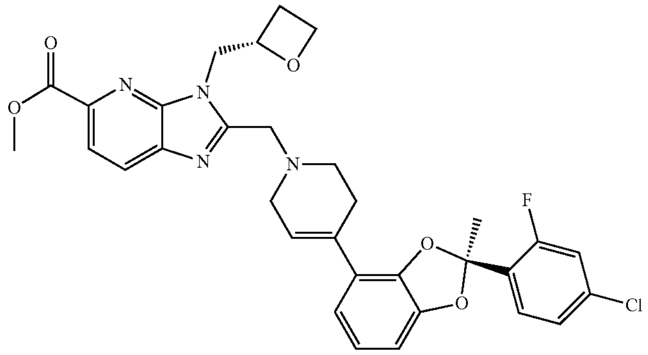 [SMILES: COC(=O)c1ccc2nc(CN3CC=C(c4cccc5c4O[C@@](C)(c4ccc(Cl)cc4F)O5)CC3)n(C[C@@H]3CCO3)c2n1]<br>7b<br>Methyl<br>2-((4-((S)-2-(4-chloro-2-fluorophenyl)-2-methylbenzo[d][1,3]dioxol-4-yl)-3,6-dihydropyridin-1(2H)-yl)methyl)-3-(((S)-oxetan-2-yl)methyl)-3H-imidazo[4,5-b]pyridine-5-carboxylate 7b |

Another aspect of the present disclosure relates to a method for preparing the compound of general formula (I) or the tautomer, mesomer, racemate, enantiomer or diastereomer thereof or the mixture thereof, or the pharmaceutically acceptable salt thereof, which comprises:

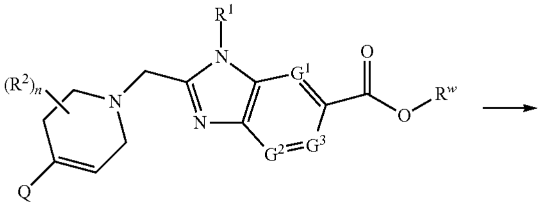

(IA)

-continued

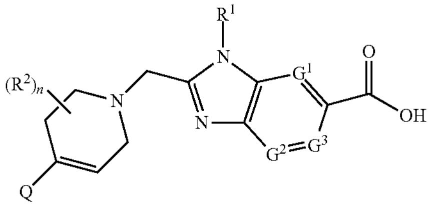

(I)

subjecting a compound of general formula (IA) to a hydrolysis reaction to obtain the compound of general formula (I), wherein:

$R^w$ is $C_{1-6}$ alkyl;

$G^1$, $G^2$, $G^3$, $R^1$, $R^2$, Q and n are as defined in general formula (I).

Another aspect of the present disclosure relates to a method for preparing a compound of general formula (II) or a tautomer, mesomer, racemate, enantiomer or diastereomer thereof or a mixture thereof, or a pharmaceutically acceptable salt thereof, which comprises:

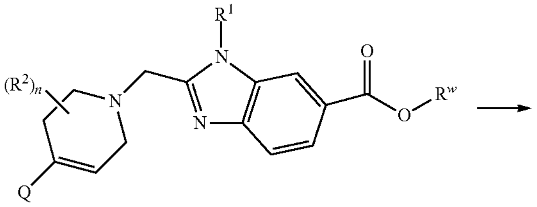

(IIA)

-continued

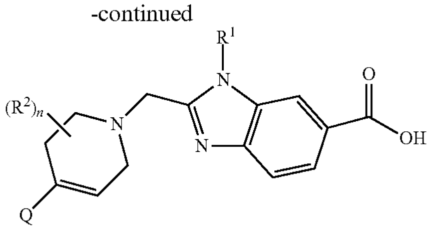

(II)

subjecting a compound of general formula (IIA) to a hydrolysis reaction to obtain the compound of general formula (II), wherein:

$R^w$ is $C_{1-6}$ alkyl;

$R^1$, $R^2$, Q and n are as defined in general formula (II).

Another aspect of the present disclosure relates to a method for preparing a compound of general formula (III) or a tautomer, mesomer, racemate, enantiomer or diastereomer thereof or a mixture thereof, or a pharmaceutically acceptable salt thereof, which comprises:

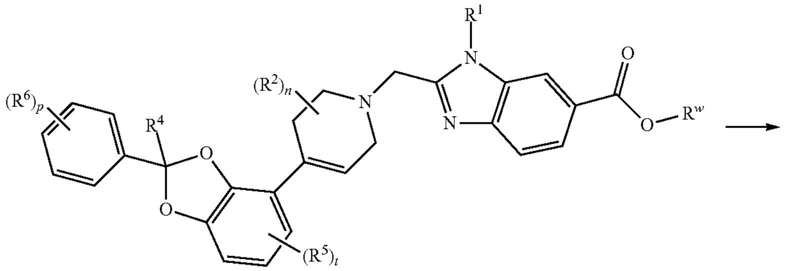

(IIIA)

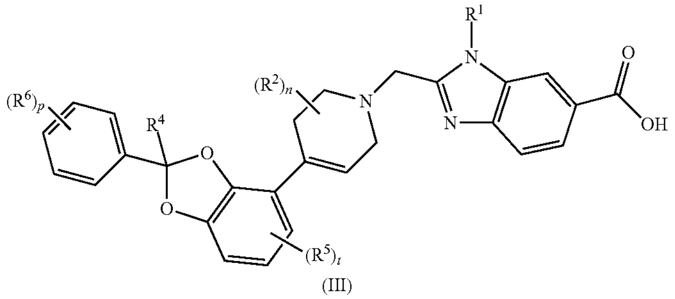

(III)

subjecting a compound of general formula (IIIA) to a hydrolysis reaction to obtain the compound of general formula (III), wherein:

$R^w$ is $C_{1-6}$ alkyl;

$R^1$, $R^2$, $R^4$-$R^6$, n, p and t are as defined in general formula (III).

Another aspect of the present disclosure relates to a method for preparing a compound of general formula (IIIaa) or a tautomer, mesomer, racemate, enantiomer or diastereomer thereof or a mixture thereof, or a pharmaceutically acceptable salt thereof, which comprises:

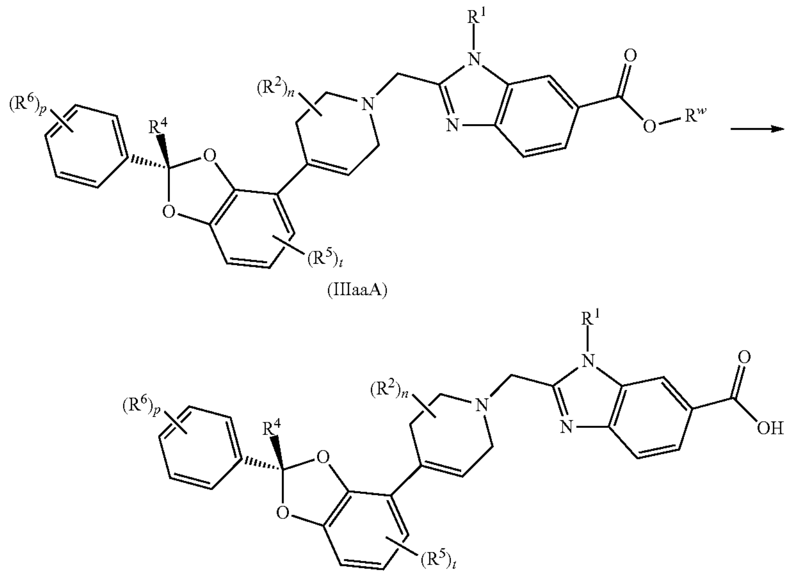

(IIIaaA)

(IIIaa)

subjecting a compound of general formula (IIIaaA) to a hydrolysis reaction to obtain the compound of general formula (IIIaa), wherein:

$R^w$ is $C_{1-6}$ alkyl;

$R^1$, $R^2$, $R^4$-$R^6$, n, p and t are as defined in general formula (IIIaa).

Another aspect of the present disclosure relates to a pharmaceutical composition, comprising the compound of general formula (I), general formula (II), general formula (III) or general formula (IIIaa) or the compounds of Table A or the tautomer, mesomer, racemate, enantiomer or diastereomer thereof or the mixture thereof, or the pharmaceutically acceptable salt thereof disclosed herein, and one or more pharmaceutically acceptable carriers, diluents or excipients.

The present disclosure further relates to use of the compound of general formula (I), general formula (II), general formula (III) or general formula (IIIaa) or the compounds of Table A or the tautomer, mesomer, racemate, enantiomer or diastereomer thereof or the mixture thereof, or the pharmaceutically acceptable salt thereof, or the pharmaceutical composition comprising the same in the preparation of a medicament for agonizing a GLP-1 receptor.

The present disclosure further relates to use of the compound of general formula (I), general formula (II), general formula (III) or general formula (IIIaa) or the compounds of Table A or the tautomer, mesomer, racemate, enantiomer or diastereomer thereof or the mixture thereof, or the pharmaceutically acceptable salt thereof, or the pharmaceutical composition comprising the same in the preparation of a medicament for treating and/or preventing type I diabetes, type II diabetes, idiopathic type I diabetes, latent autoimmune diabetes in adults (LADA), maturity-onset diabetes of the young (MODY), malnutrition-related diabetes, gestational diabetes, diabetic complications, obesity, hyperglycemia, impaired glucose intolerance, cardiovascular disease, atherosclerosis, hypertension, hyperlipidemia, coronary heart disease, cerebral infarction, stroke, nonalcoholic fatty liver disease (NAFLD), nonalcoholic steatohepatitis (NASH), Parkinson's disease, dementia, insulin resistance or hepatic insulin resistance, and preferably in the preparation of a medicament for treating and/or preventing type I diabetes, type II diabetes, obesity, diabetic complications, nonalcoholic steatohepatitis or cardiovascular disease.

The present disclosure further relates to a method for agonizing a GLP-1 receptor, which comprises administering to a patient in need thereof a therapeutically effective amount of the compound of general formula (I), general formula (II), general formula (III) or general formula (IIIaa) or compounds of Table A or the tautomer, mesomer, racemate, enantiomer or diastereomer thereof or the mixture thereof, or the pharmaceutically acceptable salt thereof, or the pharmaceutical composition comprising the same.

The present disclosure further relates to a method for treating and/or preventing type I diabetes, type II diabetes, idiopathic type I diabetes, latent autoimmune diabetes in adults (LADA), maturity-onset diabetes of the young (MODY), malnutrition-related diabetes, gestational diabetes, diabetic complications, obesity, hyperglycemia, impaired glucose intolerance, cardiovascular disease, atherosclerosis, hypertension, hyperlipidemia, coronary heart disease, cerebral infarction, stroke, nonalcoholic fatty liver disease (NAFLD), nonalcoholic steatohepatitis (NASH), Parkinson's disease, dementia, insulin resistance or hepatic insulin resistance, and preferably a method for treating and/or preventing type I diabetes, type II diabetes, obesity, diabetic complications, nonalcoholic steatohepatitis or cardiovascular disease, which comprises administering to a patient in need thereof a therapeutically effective amount of the compound of general formula (I), general formula (II), general formula (III) or general formula (IIIaa) or compounds of Table A or the tautomer, mesomer, racemate, enantiomer or diastereomer thereof or the mixture thereof, or the pharmaceutically acceptable salt thereof, or the pharmaceutical composition comprising the same.

The present disclosure further relates to the compound of general formula (I), general formula (II), general formula (III) or general formula (IIIaa) or compounds of Table A or the tautomer, mesomer, racemate, enantiomer or diastereomer thereof or the mixture thereof, or the pharmaceutically acceptable salt thereof, or the pharmaceutical composition comprising the same for use as a medicament.

The present disclosure further relates to the compound of general formula (I), general formula (II), general formula (III) or general formula (IIIaa) or compounds of Table A or the tautomer, mesomer, racemate, enantiomer or diastereomer thereof or the mixture thereof, or the pharmaceutically acceptable salt thereof, or the pharmaceutical composition comprising the same for use as a GLP-1 receptor agonist.

The present disclosure further relates to the compound of general formula (I), general formula (II), general formula (III) or general formula (IIIaa) or compounds of Table A or the tautomer, mesomer, racemate, enantiomer or diastereomer thereof or the mixture thereof, or the pharmaceutically acceptable salt thereof, or the pharmaceutical composition comprising the same for use in treating and/or preventing type I diabetes, type II diabetes, idiopathic type I diabetes, latent autoimmune diabetes in adults (LADA), maturity-onset diabetes of the young (MODY), malnutrition-related diabetes, gestational diabetes, diabetic complications, obesity, hyperglycemia, impaired glucose intolerance, cardiovascular disease, atherosclerosis, hypertension, hyperlipidemia, coronary heart disease, cerebral infarction, stroke, nonalcoholic fatty liver disease (NAFLD), nonalcoholic steatohepatitis (NASH), Parkinson's disease, dementia, insulin resistance or hepatic insulin resistance, and preferably type I diabetes, type II diabetes, obesity, diabetic complications, nonalcoholic steatohepatitis or cardiovascular disease. "Diabetic complications" are complications arising from diabetes or hyperglycemia, and may be acute or chronic complexes. The term "acute complex" includes ketoacidosis and infectious diseases (e.g., skin infection, soft tissue infection, biliary system infection, respiratory system infection and urinary tract infection), and "chronic complex" includes, for example, microangiopathy (e.g., nephropathy and retinopathy), neuropathy (e.g., sensory neuropathy, motor neuropathy and autonomic neuropathy) and gangrene. The major diabetic complexes include diabetic retinopathy, diabetic nephropathy and diabetic neuropathy.

"Coronary heart disease" includes myocardial infarction and angina pectoris.

"Dementia" includes, for example, Alzheimer's disease, (early-onset dementia) EOD, vascular dementia and diabetic dementia.

The active compounds may be formulated into a form suitable for administration by any suitable route, and one or more pharmaceutically acceptable carriers are used to formulate the compositions of the present disclosure by conventional methods. Thus, the active compounds of the present disclosure may be formulated into a variety of dosage forms for oral administration, administration by injection (e.g., intravenous, intramuscular or subcutaneous), or administration by inhalation or insufflation. The compounds of the present disclosure may also be formulated into a sustained-release dosage form, such as tablets, hard or soft capsules, aqueous or oily suspensions, emulsions, injections, dispersible powders or granules, suppositories, lozenges or syrups.

The dose of the compound or composition used in the treatment method of the present disclosure will generally vary with the severity of the disease, the body weight of the patient, and the relative efficacy of the compound. However, as a general guide, the active compound is preferably in a form of a unit dose, or in a form of a single dose that can be self-administered by a patient. The unit dose of the compound or composition of the present disclosure may be in a tablet, capsule, cachet, vial, powder, granule, lozenge, suppository, regenerating powder or liquid formulation. A suitable unit dose may be 0.1-1000 mg.

The pharmaceutical composition of the present disclosure may comprise, in addition to the active compound, one or more auxiliary materials selected from the group consisting of a filler (diluent), a binder, a wetting agent, a disintegrant, an excipient, and the like. Depending on the method of administration, the compositions may comprise 0.1 wt. % to 99 wt. % of the active compound.

The tablet comprises the active ingredient and a non-toxic pharmaceutically acceptable excipient that is used for mixing and is suitable for the preparation of the tablet. Such an excipient may be an inert excipient, a granulating agent, a disintegrant, a binder and a lubricant. Such a tablet may be uncoated or may be coated by known techniques for masking the taste of the drug or delaying the disintegration and absorption of the drug in the gastrointestinal tract and thus enabling sustained release of the drug over a longer period.

An oral formulation in a soft gelatin capsule where the active ingredient is mixed with an inert solid diluent or with a water-soluble carrier or oil vehicle may also be provided. An aqueous suspension comprises an active substance and an excipient that is used for mixing and is suitable for the preparation of the aqueous suspension. Such an excipient is a suspending agent, a dispersant or a wetting agent. The aqueous suspension may also comprise one or more preservatives, one or more colorants, one or more corrigents and one or more sweeteners.

An oil suspension may be formulated by suspending the active ingredient in a vegetable oil, or in a mineral oil. The oil suspension may comprise a thickening agent. The sweeteners and corrigents described above may be added to provide a palatable formulation. Antioxidants may also be added to preserve the compositions.

The pharmaceutical composition disclosed herein may also be in the form of an oil-in-water emulsion. The oil phase may be a vegetable oil or a mineral oil, or a mixture thereof. Suitable emulsifiers may be naturally occurring phospholipids, and the emulsion may also comprise a sweetener, a corrigent, a preservative and an antioxidant. Such a formulation may also comprise a palliative, a preservative, a colorant and an antioxidant.

The pharmaceutical composition disclosed herein may be in the form of a sterile injectable aqueous solution. Available and acceptable vehicles or solvents include water, Ringer's solution and isotonic sodium chloride solution. A sterile injectable formulation may be a sterile injectable oil-in-water microemulsion in which an active ingredient is dissolved in an oil phase. The injection or microemulsion can be locally injected into the bloodstream of a patient in large quantities. Alternatively, it may be desirable to administer solutions and microemulsions in such a way as to maintain a constant circulating concentration of the compound disclosed herein. To maintain such a constant concentration, a continuous intravenous delivery device may be used. An example of such a device is a Deltec CADD-PLUS™. 5400 intravenous injection pump.

The pharmaceutical composition disclosed herein may be in the form of a sterile injectable aqueous or oil suspension for intramuscular and subcutaneous administration. The suspension can be prepared according to the prior art using those suitable dispersants or wetting agents and suspending agents mentioned above. The sterile injectable formulation may also be a sterile injection or suspension prepared in a parenterally acceptable non-toxic diluent or solvent. In addition, a sterile fixed oil may be conventionally used as a solvent or a suspending medium. For this purpose, any blend fixed oil may be employed. In addition, fatty acids may also be used to prepare injections.

The compound of the present disclosure may be administered in the form of a suppository for rectal administration. Such a pharmaceutical composition can be prepared by mixing a drug with a suitable non-irritating excipient which is a solid at ambient temperature but a liquid in the rectum and therefore will melt in the rectum to release the drug.

The compounds of the present disclosure can be administered in the form of dispersible powders and granules that are formulated into aqueous suspensions by adding water. Such a pharmaceutical composition can be prepared by mixing the active ingredient with a dispersant or a wetting agent, a suspending agent, or one or more preservatives. As is well known to those skilled in the art, the dose of the drug administered depends on a variety of factors, including but not limited to, the activity of the particular compound employed, the age of the patient, the weight of the patient, the health condition of the patient, the behavior of the patient, the diet of the patient, the time of administration, the route of administration, the rate of excretion, the combination of drugs, and the like. In addition, the optimal treatment regimen, such as the mode of administration, the daily dose of the compound or the type of pharmaceutically acceptable salts, can be verified according to conventional treatment regimens.

Description of the Terms

Unless otherwise stated, the terms used in the specification and claims have the following meanings.

The term "alkyl" refers to a saturated aliphatic hydrocarbon group which is a linear or branched group containing 1 to 20 carbon atoms, preferably alkyl containing 1 to 12 (e.g., 1, 2, 3, 4, 5, 6, 7, 8, 9, 10, 11 and 12) carbon atoms, and more preferably alkyl containing 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof, etc. More preferred is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl may be substituted or unsubstituted. When substituted, the substituent may be substituted at any available connection site, and the substituent is preferably one or more substituents independently optionally selected from the group consisting of a D atom, halogen, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "alkylene" refers to a saturated linear or branched aliphatic hydrocarbon group, which is a residue derived from the parent alkane by removal of two hydrogen atoms from the same carbon atom or two different carbon atoms. It is a linear or branched group containing 1 to 20 carbon atoms, preferably alkylene containing 1 to 12 (e.g., 1, 2, 3, 4, 5, 6, 7, 8, 9, 10, 11 and 12) carbon atoms, and more preferably alkylene containing 1 to 6 carbon atoms. Non-limiting examples of alkylene include, but are not limited to, methylene ($-CH_2-$), 1,1-ethylene ($-CH(CH_3)-$), 1,2-ethylene ($-CH_2CH_2-$), 1,1-propylene ($-CH(CH_2CH_3)-$), 1,2-propylene ($-CH_2CH(CH_3)-$), 1,3-propylene ($-CH_2CH_2CH_2-$), 1,4-butylene ($-CH_2CH_2CH_2CH_2-$), etc. The alkylene may be substituted or unsubstituted. When substituted, the substituent may be substituted at any available connection site, and the substituent is preferably one or more substituents independently optionally selected from the group consisting of alkenyl, alkynyl, alkoxy, haloalkoxy, cycloalkyloxy, heterocyclyloxy, alkylthio, alkylamino, halogen, mercapto, hydroxy, nitro, cyano, cycloalkyl, heterocyclyl, aryl, heteroaryl, cycloalkoxy, heterocycloalkoxy, cycloalkylthio, heterocycloalkylthio and oxo.

The term "alkenyl" refers to an alkyl compound containing at least one carbon-carbon double bond in the molecule, wherein the alkyl is defined as above. Alkenyl may be substituted or unsubstituted. When substituted, the substituent is preferably one or more groups independently selected from the group consisting of alkoxy, halogen, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "alkynyl" refers to an alkyl compound containing at least one carbon-carbon triple bond in the molecule, wherein the alkyl is defined as above. Alkynyl may be substituted or unsubstituted. When substituted, the substituent is preferably one or more groups independently selected from the group consisting of alkoxy, halogen, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "cycloalkyl" refers to a saturated or partially unsaturated monocyclic or polycyclic hydrocarbon substituent. The cycloalkyl ring contains 3 to 20 carbon atoms, preferably 3 to 12 carbon atoms, more preferably 3 to 8 (e.g., 3, 4, 5, 6, 7 and 8) carbon atoms, and most preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes spiro cycloalkyl, fused cycloalkyl, and bridged cycloalkyl.

The term "spiro cycloalkyl" refers to a 5- to 20-membered polycyclic group in which monocyclic rings share one carbon atom (referred to as the spiro atom), wherein the spiro cycloalkyl may contain one or more double bonds. Preferably, the spiro cycloalkyl is 6- to 14-membered, and more preferably 7- to 10-membered (e.g., 7-membered, 8-membered, 9-membered or 10-membered). According to the number of the spiro atoms shared among the rings, the spiro cycloalkyl may be monospiro cycloalkyl, bispiro cycloalkyl or polyspiro cycloalkyl, preferably monospiro cycloalkyl and bispiro cycloalkyl, and more preferably 3-membered/5-membered, 3-membered/6-membered, 4-membered/4-membered, 4-membered/5-membered, 4-membered/6-membered, 5-membered/5-membered or 5-membered/6-membered monospiro cycloalkyl. Non-limiting examples of spiro cycloalkyl include:

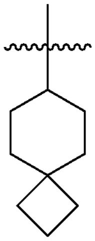
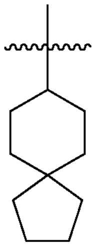
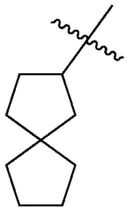
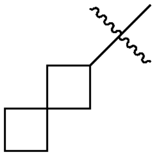
and
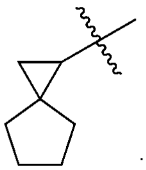
.

The term "fused cycloalkyl" refers to a 5- to 20-membered carbon polycyclic group in which each ring shares a pair of adjacent carbon atoms with the other rings in the system, wherein one or more of the rings may contain one or more double bonds. Preferably, the fused cycloalkyl is 6- to 14-membered, and more preferably 7- to 10-membered (e.g., 7-membered, 8-membered, 9-membered or 10-membered). According to the number of the formed rings, the fused cycloalkyl may be bicyclic, tricyclic, tetracyclic or polycyclic fused cycloalkyl, preferably bicyclic or tricyclic fused cycloalkyl, and more preferably 3-membered/4-membered, 3-membered/5-membered, 3-membered/6-membered, 4-membered/4-membered, 4-membered/5-membered, 4-membered/6-membered, 5-membered/4-membered, 5-membered/5-membered, 5-membered/6-membered, 6-membered/3-membered, 6-membered/4-membered, 6-membered/5-membered and 6-membered/6-membered bicyclic fused cycloalkyl. Non-limiting examples of fused cycloalkyl include:

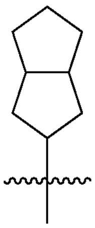
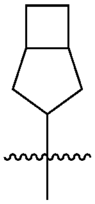
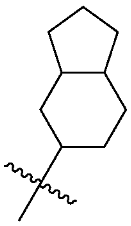
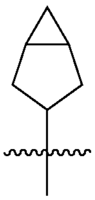
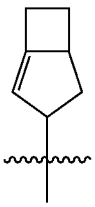
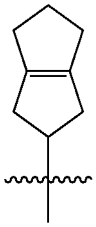

-continued

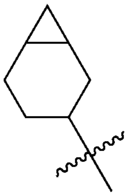
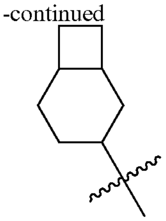
and
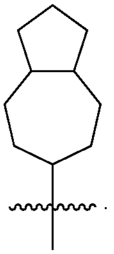
.

The term "bridged cycloalkyl" refers to a 5- to 20-membered carbon polycyclic group in which any two rings share two carbon atoms that are not directly connected to each other, wherein the bridged cycloalkyl may contain one or more double bonds. Preferably, the bridged cycloalkyl is 6- to 14-membered, and more preferably 7- to 10-membered (e.g., 7-membered, 8-membered, 9-membered or 10-membered). According to the number of the formed rings, the bridged cycloalkyl may be bicyclic, tricyclic, tetracyclic or polycyclic, preferably bicyclic, tricyclic or tetracyclic, and more preferably bicyclic or tricyclic. Non-limiting examples of bridged cycloalkyl include:

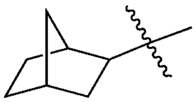
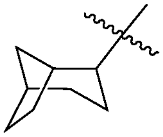
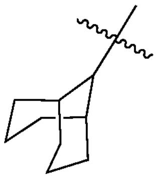
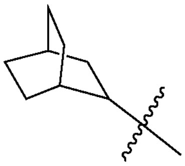
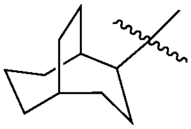
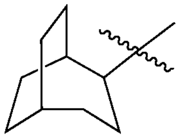
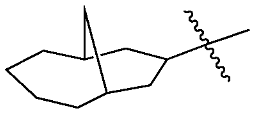
and
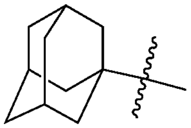
.

The cycloalkyl ring includes those in which the cycloalkyl described above (including monocyclic, spiro, fused and bridged rings) is fused to an aryl, heteroaryl or heterocycloalkyl ring, wherein the ring connected to the parent structure is cycloalkyl. Non-limiting examples include indanyl, tetrahydronaphthyl, benzocycloheptenyl, and the like, and preferably indanyl and tetrahydronaphthyl.

The cycloalkyl may be substituted or unsubstituted. When substituted, the substituent may be substituted at any available connection site, and the substituent is preferably one or more substituents independently optionally selected from the group consisting of halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "alkoxy" refers to —O-(alkyl), wherein the alkyl is defined as above. Non-limiting examples of alkoxy include methoxy, ethoxy, propoxy and butoxy. Alkoxy may be optionally substituted or unsubstituted. When substituted, the substituent is preferably one or more groups independently selected from the group consisting of a D atom, halogen, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "heterocyclyl" refers to a saturated or partially unsaturated monocyclic or polycyclic hydrocarbon substituent containing 3 to 20 ring atoms, wherein one or more of the ring atoms are heteroatoms selected from the group consisting of nitrogen, oxygen, sulfur, S(O) and $S(O)_2$, excluding a cyclic portion of —O—O—, —O—S— or —S—S—, and the remaining ring atoms are carbon atoms. The heterocyclyl preferably contains 3 to 12 (e.g., 3, 4, 5, 6, 7, 8, 9, 10, 11 and 12) ring atoms, of which 1 to 4 (e.g., 1, 2, 3 and 4) are heteroatoms; more preferably 3 to 8 (e.g., 3, 4, 5, 6, 7 and 8) ring atoms, of which 1 to 3 (e.g., 1, 2 and 3) are heteroatoms; more preferably 3 to 6 ring atoms, of which 1 to 3 are heteroatoms; most preferably 5 or 6 ring atoms, of which 1 to 3 are heteroatoms. Non-limiting examples of monocyclic heterocyclyl include oxetanyl, pyrrolidinyl, tetrahydropyranyl, 1,2,3,6-tetrahydropyridinyl, piperidinyl, piperazinyl, morpholinyl, thiomorpholinyl, homopiperazinyl, and the like. Non-limiting examples of polycyclic heterocyclyl include spiro heterocyclyl, fused heterocyclyl, and bridged heterocyclyl.

The term "spiro heterocyclyl" refers to a 5- to 20-membered polycyclic heterocyclyl group in which monocyclic rings share one atom (referred to as the spiro atom), wherein one or more ring atoms are heteroatoms selected from the group consisting of nitrogen, oxygen, sulfur, S(O) and $S(O)_2$, and the remaining ring atoms are carbon atoms. The spiro heterocyclyl may contain one or more double bonds. Preferably, the spiro heterocyclyl is 6- to 14-membered, and more preferably 7- to 10-membered (e.g., 7-membered, 8-membered, 9-membered or 10-membered). According to the number of spiro atoms shared among the rings, the spiro heterocyclyl may be monospiro heterocyclyl, bispiro heterocyclyl or polyspiro heterocyclyl, preferably monospiro heterocyclyl and bispiro heterocyclyl, and more preferably 4-membered/4-membered, 4-membered/5-membered, 4-membered/6-membered, 5-membered/5-membered or 5-membered/6-membered monospiro heterocyclyl. Non-limiting examples of spiro heterocyclyl include:

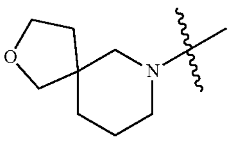

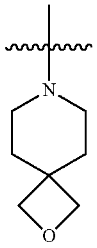

-continued

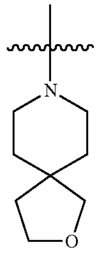

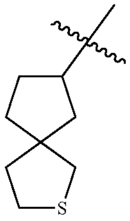

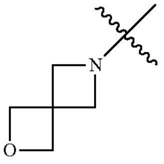

and

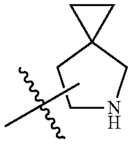

.

The term "fused heterocyclyl" refers to a 5- to 20-membered polycyclic heterocyclyl group in which each ring shares a pair of adjacent atoms with the other rings in the system, wherein one or more of the rings may contain one or more double bonds. In the fused heterocyclyl, one or more of the ring atoms are heteroatoms selected from the group consisting of nitrogen, oxygen, sulfur, S(O) and $S(O)_2$, and the remaining ring atoms are carbon atoms. Preferably, the fused heterocyclyl is 6- to 14-membered, and more preferably 7- to 10-membered (e.g., 7-membered, 8-membered, 9-membered or 10-membered). According to the number of the formed rings, the fused heterocyclyl may be bicyclic, tricyclic, tetracyclic or polycyclic fused heterocyclyl, preferably bicyclic or tricyclic fused heterocyclyl, and more preferably 3-membered/4-membered, 3-membered/5-membered, 3-membered/6-membered, 4-membered/4-membered, 4-membered/5-membered, 4-membered/6-membered, 5-membered/4-membered, 5-membered/5-membered, 5-membered/6-membered, 6-membered/3-membered, 6-membered/4-membered, 6-membered/5-membered and 6-membered/6-membered bicyclic fused heterocyclyl. Non-limiting examples of fused heterocyclyl include:

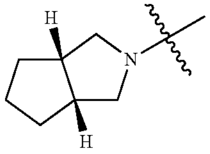

,

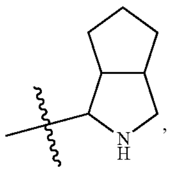

,

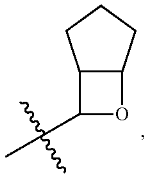

,

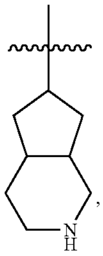

,

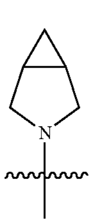

,

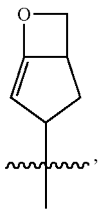

,

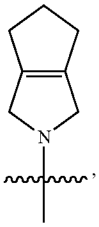

,

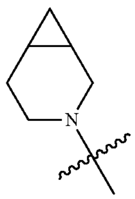

,

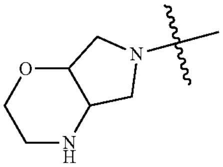

,

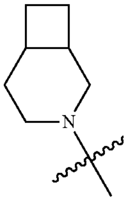

,

-continued

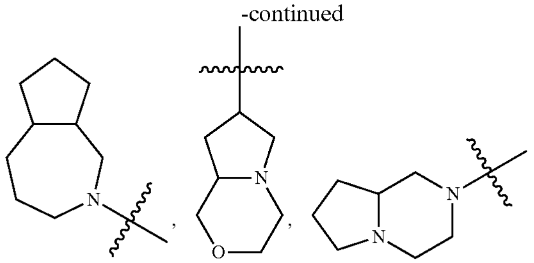

and

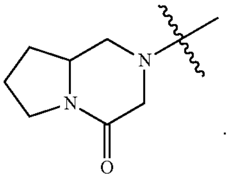

The term “bridged heterocyclyl” refers to a 5- to 14-membered polycyclic heterocyclyl group in which any two rings share two carbon atoms that are not directly connected to each other, wherein the bridged heterocyclyl may contain one or more double bonds. In the bridged heterocyclyl, one or more of the ring atoms are heteroatoms selected from the group consisting of nitrogen, oxygen, sulfur, S(O) and $S(O)_2$, and the remaining ring atoms are carbon atoms. Preferably, the bridged heterocyclyl is 6- to 14-membered, and more preferably 7- to 10-membered (e.g., 7-membered, 8-membered, 9-membered or 10-membered). According to the number of the formed rings, the bridged heterocyclyl may be bicyclic, tricyclic, tetracyclic or polycyclic, preferably bicyclic, tricyclic or tetracyclic, and more preferably bicyclic or tricyclic. Non-limiting examples of bridged heterocyclyl include:

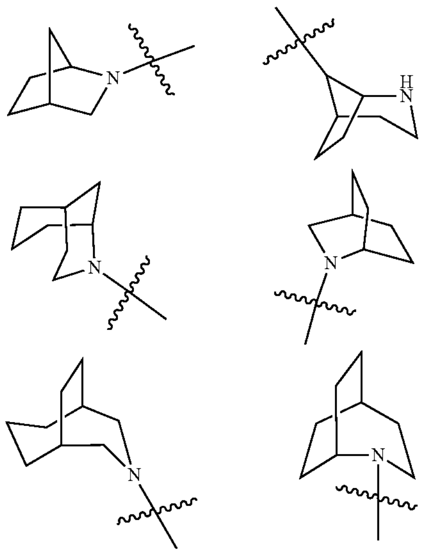

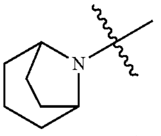

and

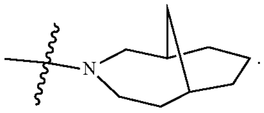

The heterocyclyl ring includes those in which the heterocyclyl described above (including monocyclic, spiro heterocyclic, fused heterocyclic and bridged heterocyclic rings) is fused to an aryl, heteroaryl or cycloalkyl ring, wherein the ring connected to the parent structure is heterocyclyl. Non-limiting examples include:

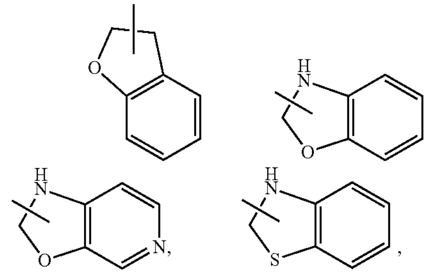

etc.

The heterocyclyl may be substituted or unsubstituted. When substituted, the substituent may be substituted at any available connection site, and the substituent is preferably one or more substituents independently optionally selected from the group consisting of halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term “aryl” refers to a 6- to 14-membered, preferably 6- to 10-membered carbon monocyclic or fused polycyclic (fused polycyclic rings are those sharing a pair of adjacent carbon atoms) group having a conjugated π-electron system, such as phenyl and naphthyl. The aryl ring includes those in which the aryl ring described above is fused to a heteroaryl, heterocyclyl or cycloalkyl ring, wherein the ring connected to the parent structure is an aryl ring. Non-limiting examples include:

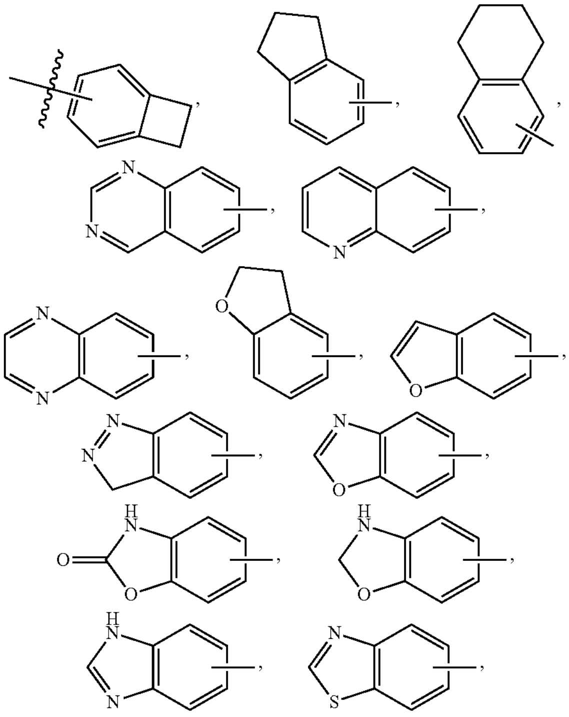

-continued

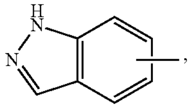,
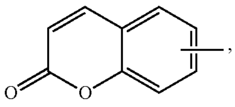, and
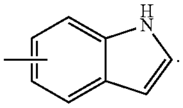.

The aryl may be substituted or unsubstituted. When substituted, the substituent may be substituted at any available connection site, and the substituent is preferably one or more substituents independently optionally selected from the group consisting of halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "heteroaryl" refers to a heteroaromatic system containing 1 to 4 (e.g., 1, 2, 3 and 4) heteroatoms and 5 to 14 ring atoms, wherein the heteroatoms are selected from the group consisting of oxygen, sulfur and nitrogen. The heteroaryl is preferably 5- to 10-membered (e.g., 5-membered, 6-membered, 7-membered, 8-membered, 9-membered or 10-membered) and more preferably 5-membered or 6-membered, e.g., furanyl, thienyl, pyridinyl, pyrrolyl, N-alkylpyrrolyl, pyrimidinyl, pyrazinyl, pyridazinyl, imidazolyl, pyrazolyl, triazolyl and tetrazolyl. The heteroaryl ring includes those in which the heteroaryl ring described above is fused to an aryl, heterocyclyl or cycloalkyl ring, wherein the ring connected to the parent structure is a heteroaryl ring. Non-limiting examples include:

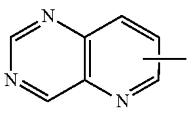
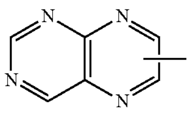
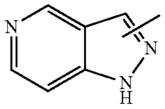
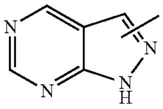
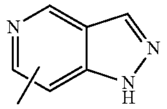
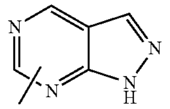
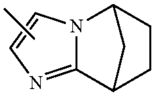
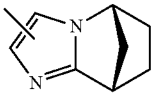
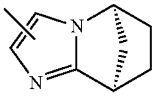
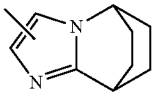
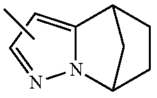
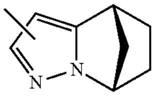
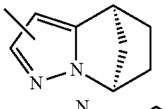
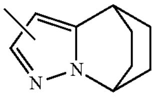
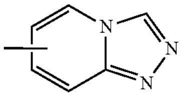
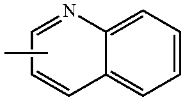
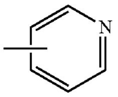
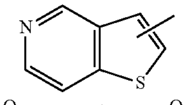
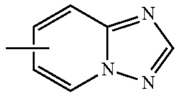
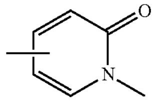
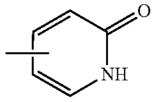
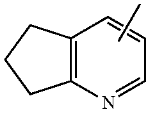
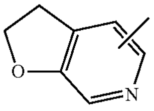
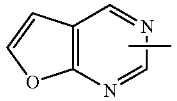

-continued

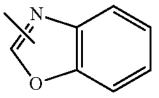
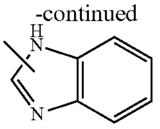
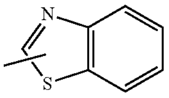
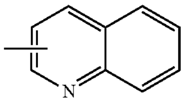
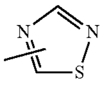
and
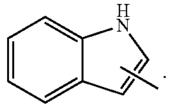.

The heteroaryl may be substituted or unsubstituted. When substituted, the substituent may be substituted at any available connection site, and the substituent is preferably one or more substituents independently optionally selected from the group consisting of halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The cycloalkyl, heterocyclyl, aryl and heteroaryl described above include residues derived from the parent ring by removal of one hydrogen atom from a ring atom, or residues derived from the parent ring by removal of two hydrogen atoms from the same ring atom or two different ring atoms, i.e., "divalent cycloalkyl", "divalent heterocyclyl", "arylene" or "heteroarylene".

The term "amino protecting group" refers to a group that can be easily removed and is intended to protect an amino group from being changed when a reaction is conducted elsewhere in the molecule. Non-limiting examples include (trimethylsilyl)ethoxymethyl, tetrahydropyranyl, tert-butoxycarbonyl, acetyl, benzyl, allyl, p-methoxybenzyl, and the like. These groups may be optionally substituted with 1 to 3 substituents selected from the group consisting of halogen, alkoxy and nitro. The amino protecting groups are preferably (trimethylsilyl)ethoxymethyl and tert-butoxycarbonyl.

The term "hydroxy protecting group" is a suitable group known in the art for protecting hydroxy. See the hydroxy protecting groups in the literature ("*Protective Groups in Organic Synthesis*", $5^{th}$ Ed. T. W. Greene & P. G. M. Wuts). As an example, preferably, the hydroxy protecting group may be ($C_{1-10}$ alkyl or aryl)$_3$silyl, e.g., triethylsilyl, triisopropylsilyl, tert-butyldimethylsilyl or tert-butyldiphenylsilyl; $C_{1-10}$ alkyl or substituted alkyl, preferably alkoxy or aryl-substituted alkyl, more preferably $C_{1-6}$ alkoxy-substituted $C_{1-6}$ alkyl or phenyl-substituted $C_{1-6}$ alkyl, and most preferably $C_{1-4}$ alkoxy-substituted $C_{1-4}$ alkyl, e.g., methyl, tert-butyl, allyl, benzyl, methoxymethyl (MOM), ethoxyethyl or 2-tetrahydropyranyl (THP); ($C_{1-10}$ alkyl or aryl) acyl, e.g., formyl, acetyl, benzoyl or p-nitrobenzoyl; ($C_{1-6}$ alkyl or $C_{6-10}$ aryl)sulfonyl; or ($C_{1-6}$ alkoxy or $C_{6-10}$ aryloxy) carbonyl. The hydroxy protecting group is preferably p-nitrobenzoyl.

The term "cycloalkyloxy" refers to cycloalkyl-O—, wherein the cycloalkyl is defined as above.

The term "heterocyclyloxy" refers to heterocyclyl-O—, wherein the heterocyclyl is defined as above.

The term "alkylthio" refers to alkyl-S—, wherein the alkyl is defined as above.

The term "haloalkyl" refers to alkyl substituted with one or more halogens, wherein the alkyl is defined as above.

The term "haloalkoxy" refers to alkoxy substituted with one or more halogens, wherein the alkoxy is defined as above.

The term "deuterated alkyl" refers to alkyl substituted with one or more deuterium atoms, wherein the alkyl is defined as above.

The term "hydroxyalkyl" refers to alkyl substituted with one or more hydroxy groups, wherein the alkyl is defined as above.

The term "halogen" refers to fluorine, chlorine, bromine or iodine.

The term "hydroxy" refers to —OH.

The term "mercapto" refers to —SH.

The term "amino" refers to $—NH_2$.

The term "cyano" refers to —CN.

The term "nitro" refers to $—NO_2$.

The term "oxo" refers to "=O".

The term "carbonyl" refers to C=O.

The term "carboxyl" refers to —C(O)OH.

The term "carboxylate" refers to —C(O)O(alkyl), —C(O)O(cycloalkyl), (alkyl)C(O)O— or (cycloalkyl)C(O)O—, wherein the alkyl and cycloalkyl are defined as above.

The present disclosure also comprises various deuterated forms of the compound of formula (I). Each available hydrogen atom connected to a carbon atom may be independently replaced with a deuterium atom. Those skilled in the art are able to synthesize the deuterated forms of the compound of general formula (I) with reference to the relevant literature. Commercially available deuterated starting materials can be used in preparing the deuterated forms of the compound of formula (I), or they can be synthesized using conventional techniques with deuterated reagents including, but not limited to, deuterated borane, tri-deuterated borane in tetrahydrofuran, deuterated lithium aluminum hydride, deuterated iodoethane, deuterated iodomethane, and the like. Deuterides can generally retain comparable activity to non-deuterated compounds and can achieve better metabolic stability when deuterated at certain specific sites, thereby achieving certain therapeutic advantages.

The term "optional" or "optionally" means that the event or circumstance subsequently described may, but not necessarily, occur, and that the description includes instances where the event or circumstance occurs or does not occur. For example, "heterocyclyl groups optionally substituted with alkyl" means that alkyl may be, but not necessarily, present, and that the description includes instances where the heterocyclyl groups are or are not substituted with the alkyl.

The term "substituted" means that one or more, preferably 1-5, more preferably 1-3 hydrogen atoms in the group are independently substituted with a corresponding number of substituents. Those skilled in the art are able to determine (experimentally or theoretically) possible or impossible substitution without undue efforts. For example, it may be unstable when an amino or hydroxy group having a free hydrogen is bound to a carbon atom having an unsaturated (e.g., olefinic) bond.

The term "pharmaceutical composition" refers to a mixture containing one or more of the compounds described herein or a physiologically/pharmaceutically acceptable salt or pro-drug thereof, and other chemical components, and other components, for example, physiologically/pharmaceutically acceptable carriers and excipients. The purpose of the pharmaceutical composition is to promote the administration to an organism, which facilitates the absorption of the active ingredient, thereby exerting biological activities.

The term "pharmaceutically acceptable salt" refers to salts of the compounds disclosed herein, which are safe and effective for use in the body of a mammal and possess the requisite biological activities. The salts may be prepared separately during the final separation and purification of the compound, or by reacting an appropriate group with an appropriate base or acid. Bases commonly used to form pharmaceutically acceptable salts include inorganic bases such as sodium hydroxide and potassium hydroxide, and organic bases such as ammonia. Acids commonly used to form pharmaceutically acceptable salts include inorganic acids and organic acids.

For drugs and pharmacological active agents, the term "therapeutically effective amount" refers to an amount of a medicament or an agent that is sufficient to provide the desired effect but is non-toxic. The determination of the effective amount varies from person to person. It depends on the age and general condition of a subject, as well as the particular active substance used. The appropriate effective amount in a case may be determined by those skilled in the art in the light of routine tests.

The term "pharmaceutically acceptable" as used herein means that those compounds, materials, compositions and/or dosage forms which are, within the scope of reasonable medical judgment, suitable for use in contact with the tissues of patients without excessive toxicity, irritation, allergic reaction, or other problems or complications, and are commensurate with a reasonable benefit/risk ratio and effective for the intended use. As used herein, the singular forms "a", "an" and "the" include plural references and vice versa, unless otherwise clearly defined in the context.

When the term "about" is applied to parameters such as pH, concentration and temperature, it means that the parameter may vary by ±10%, and sometimes more preferably within ±5%. As will be appreciated by those skilled in the art, when the parameters are not critical, the numbers are generally given for illustrative purposes only and are not intended to be limiting.

The compound disclosed herein may also include an isotopic derivative thereof. The term "isotopic derivative" refers to compounds that differ in structure only by having one or more enriched isotopic atoms. For example, compounds with the structure disclosed herein having "deuterium" or "tritium" in place of hydrogen, or $^{18}F$-fluorine labeling ($^{18}F$ isotope) in place of fluorine, or $^{11}C$-, $^{13}C$- or $^{14}C$-enriched carbon ($^{11}C$-, $^{13}C$- or $^{14}C$-carbon labeling; $^{11}C$-, $^{13}C$- or $^{14}C$-isotope) in place of a carbon atom are within the scope of the present disclosure. Such a compound can be used as an analytical tool or a probe in, for example, a biological assay, or may be used as a tracer for in vivo diagnostic imaging of disease, or as a tracer in a pharmacodynamic, pharmacokinetic or receptor study.

Synthesis Method of Compounds Disclosed Herein

In order to achieve the purpose of the present disclosure, the following technical schemes are adopted in the present disclosure:

Scheme 1

Provided is a method for preparing the compound of general formula (I) or the tautomer, mesomer, racemate, enantiomer or diastereomer thereof or the mixture thereof, or the pharmaceutically acceptable salt thereof of the present disclosure, which comprises the following step:

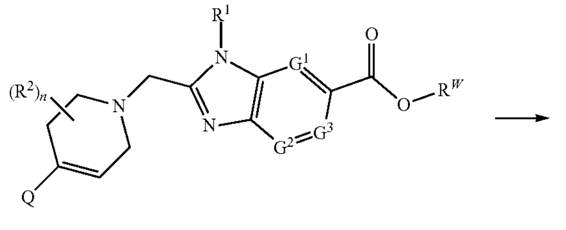

(IA)

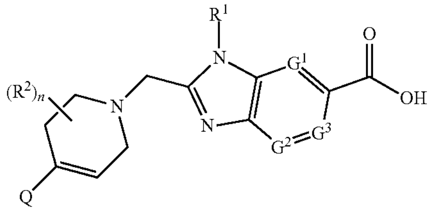

(I)

subjecting a compound of general formula (IA) to a hydrolysis reaction in the presence of a basic reagent to obtain the compound of general formula (I), wherein:

$R^w$ is $C_{1-6}$ alkyl;

$G^1$, $G^2$, $G^3$, $R^1$, $R^2$, Q and n are as defined in general formula (I).

Scheme 2

Provided is a method for preparing the compound of general formula (II) or the tautomer, mesomer, racemate, enantiomer or diastereomer thereof or the mixture thereof, or the pharmaceutically acceptable salt thereof of the present disclosure, which comprises the following step:

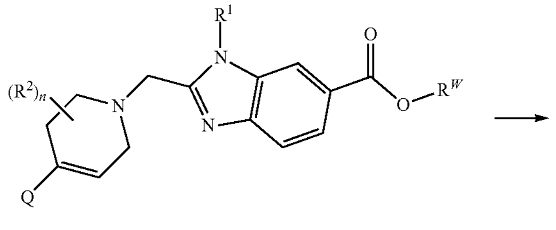

(IIA)

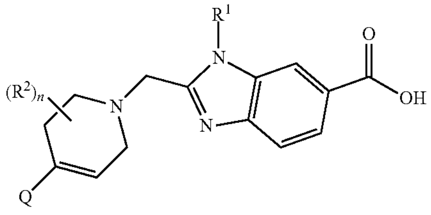

(II)

subjecting a compound of general formula (IIA) to a hydrolysis reaction in the presence of a basic reagent to obtain the compound of general formula (II), wherein:

$R^w$ is $C_{1-6}$ alkyl;

$R^1$, $R^2$, Q and n are as defined in general formula (II).

Scheme 3

Provided is a method for preparing the compound of general formula (III) or the tautomer, mesomer, racemate, enantiomer or diastereomer thereof or the mixture thereof, or the pharmaceutically acceptable salt thereof of the present disclosure, which comprises the following step:

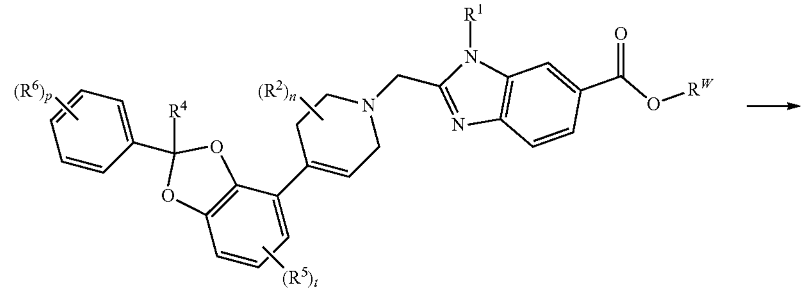

(IIIA)

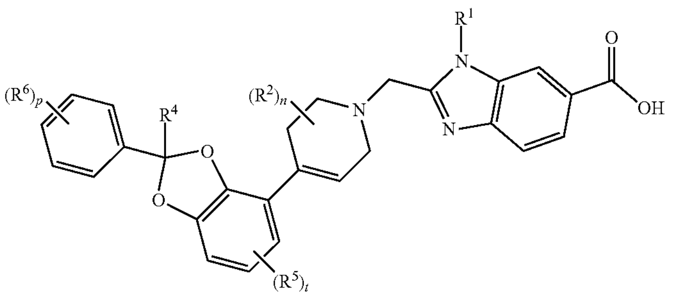

(III)

subjecting a compound of general formula (IIIA) to a hydrolysis reaction in the presence of a basic reagent to obtain the compound of general formula (III), wherein:

$R^w$ is $C_{1-6}$ alkyl;

$R^1$, $R^2$, $R^4$-$R^6$, n, p and t are as defined in general formula (III).

Scheme 4

Provided is a method for preparing the compound of general formula (IIIaa) or the tautomer, mesomer, racemate, enantiomer or diastereomer thereof or the mixture thereof, or the pharmaceutically acceptable salt thereof of the present disclosure, which comprises the following step:

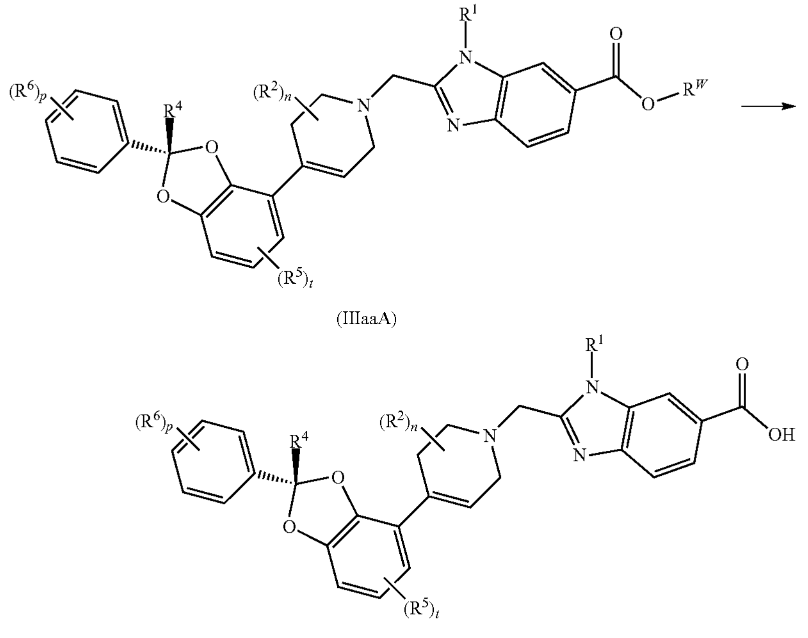

(IIIaaA)

(IIIaa)

subjecting a compound of general formula (IIIaaA) to a hydrolysis reaction in the presence of a basic reagent to obtain the compound of general formula (IIIaa), wherein:

$R^w$ is $C_{1-6}$ alkyl;

$R^1$, $R^2$, $R^4$-$R^6$, n, p and t are as defined in general formula (IIIaa).

The basic reagents of the above schemes 1 to 4 include organic bases and inorganic bases, wherein the organic bases include, but are not limited to, triethylamine, N,N-diisopropylethylamine, n-butyllithium, lithium diisopropylamide, potassium acetate, sodium tert-butoxide or potassium tert-butoxide, and the inorganic bases include, but are not limited to, sodium hydride, potassium phosphate, sodium carbonate, sodium acetate, potassium acetate, potassium carbonate or cesium carbonate, sodium hydroxide, lithium hydroxide monohydrate, lithium hydroxide and potassium hydroxide, and preferably lithium hydroxide or lithium hydroxide monohydrate.

The above reactions are preferably conducted in a solvent including, but not limited to: ethylene glycol dimethyl ether, acetic acid, methanol, ethanol, acetonitrile, n-butanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

DETAILED DESCRIPTION

The following examples further illustrate the present disclosure, but the present disclosure is not limited thereto.

EXAMPLES

The structure of the compound was determined by nuclear magnetic resonance (NMR) spectroscopy and/or mass spectrometry (MS). NMR shift (δ) is given in a unit of $10^{-6}$ (ppm). NMR spectra were measured using a Bruker AVANCE-400 nuclear magnetic resonance instrument, with deuterated dimethyl sulfoxide (DMSO-$d_6$), deuterated chloroform ($CDCl_3$) and deuterated methanol ($CD_3OD$) as determination solvents and tetramethylsilane (TMS) as internal standard.

MS analysis was performed using a FINNIGAN LCQAd (ESI) mass spectrometer (manufacturer: Thermo, model: Finnigan LCQ advantage MAX).

High performance liquid chromatography (HPLC) analysis was performed using the following HPLC instruments: Agilent HPLC 1200DAD, Agilent HPLC 1200VWD and Waters HPLC e2695-2489.

Chiral HPLC analysis was performed using Agilent 1260 DAD HPLC.

HPLC preparation was performed using Waters 2767, Waters 2767-SQ Detecor2, Shimadzu LC-20AP and Gilson-281 preparative chromatographs.

Chiral preparation was performed using a Shimadzu LC-20AP preparative chromatograph.

A CombiFlash Rf200 (TELEDYNE ISCO) system was used for rapid preparation.

Huanghai HSGF254 or Qingdao GF254 silica gel plates of specifications 0.15 mm to 0.2 mm were adopted for thin layer chromatography (TLC) analysis and 0.4 mm to 0.5 mm for TLC separation and purification.

The silica gel column chromatography generally used 200 to 300-mesh silica gel (Huanghai, Yantai) as the carrier.

The mean inhibition of kinase and the $IC_{50}$ value were measured using a NovoStar microplate reader (BMG, Germany).

Known starting materials described herein may be synthesized using or according to methods known in the art, or may be purchased from ABCR GmbH & Co. KG, Acros Organics, Aldrich Chemical Company, Accela ChemBio Inc., Chembee Chemicals, and other companies.

In the examples, the reactions can be performed in an argon atmosphere or a nitrogen atmosphere unless otherwise specified.

The argon atmosphere or nitrogen atmosphere means that the reaction flask is connected to a balloon containing about 1 L of argon or nitrogen.

The hydrogen atmosphere means that the reaction flask is connected to a balloon containing about 1 L of hydrogen.

Parr 3916EKX hydrogenator, Qinglan QL-500 hydrogenator or HC2-SS hydrogenator was used in the pressurized hydrogenation reactions.

The hydrogenation reactions usually involve 3 cycles of vacuumization and hydrogen purge.

A CEM Discover-S 908860 microwave reactor was used in the microwave reactions.

In the examples, a solution refers to an aqueous solution unless otherwise specified.

In the examples, the reaction temperature was room temperature, i.e., 20° C. to 30° C., unless otherwise specified.

The monitoring of the reaction progress in the examples was conducted by thin layer chromatography (TLC). The developing solvent for reactions, the eluent system for column chromatography purification and the developing solvent system for thin layer chromatography included: A: dichloromethane/methanol system, B: n-hexane/ethyl acetate system, C: n-hexane/dichloromethane system, and D: ethyl acetate/dichloromethane/n-hexane. The volume ratio of the solvents was adjusted according to the polarity of the compound, or by adding a small amount of basic or acidic reagents such as triethylamine and acetic acid.

TsOH is p-toluenesulfonic acid.

Example 1

(S)-2-((6-((4-cyano-2-fluorobenzyl)oxy-3',6'-dihydro-[2,4'-bipyridin]-1'(2'H)-yl)methyl)-1-(oxetan-2-ylmethyl)-1H-benzo[d]imidazole-6-carboxylic acid 1

1

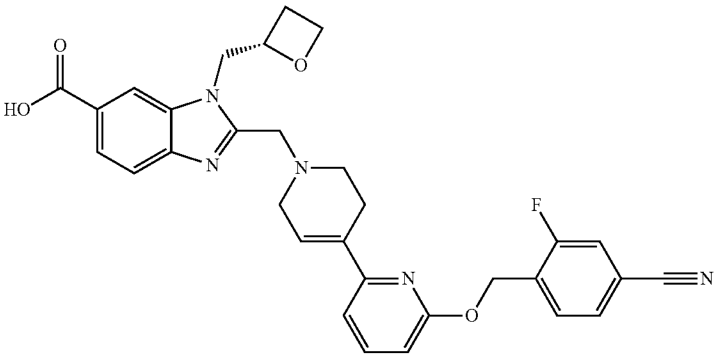

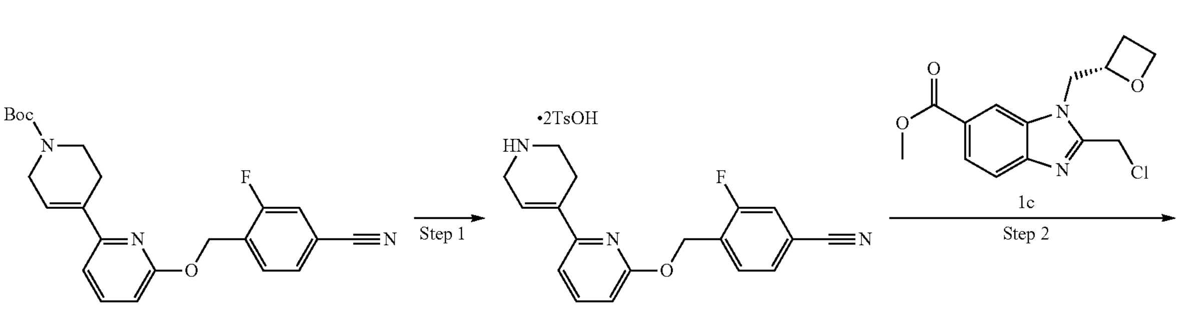

1a

1b

-continued

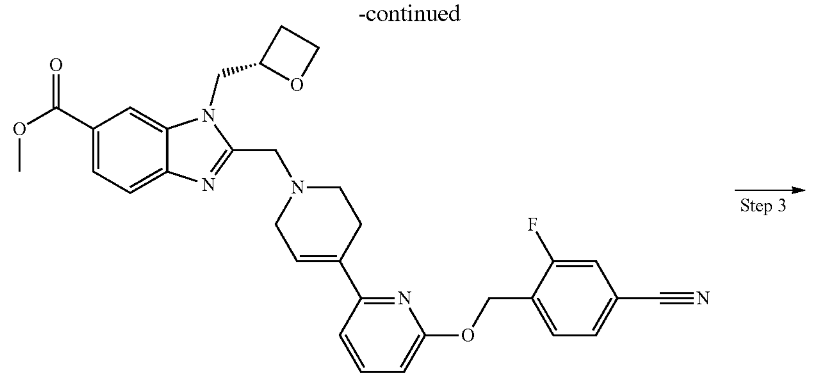

1d

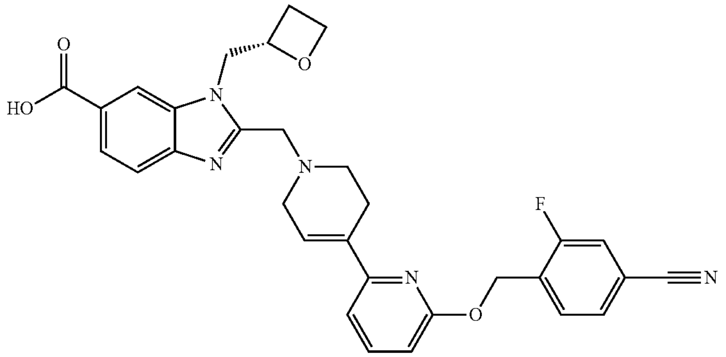

1

Step 1

3-fluoro-4-((1',2',3',6'-tetrahydro-[2,4'-bipyridin]-6-yl)oxy)methyl)benzonitrile 1b Tert-Butyl 6-((4-cyano-2-fluorobenzyl)oxy)-3',6'-dihydro-[2,4'-bipyridine]-1'(2'H)-carboxylate 1a (96 mg, 234.4595 μmol, prepared using the method disclosed in intermediate 4 on page 51 of the specification in patent application "WO2018109607") was dissolved in ethyl acetate (5 mL), followed by addition of p-toluenesulfonic acid monohydrate (133 mg, 699.2014 μmol), and the reaction solution was stirred at 60° C. for 4 h, cooled, filtered, and washed with ethyl acetate (10 mL). The organic phase was collected, dried, filtered, and concentrated under reduced pressure to give compound 1b (126 mg), which was directly used in the next step without purification.

MS m/z (ESI): 310.1 [M+1].

Step 2

Methyl (S)-2-((6-((4-cyano-2-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylate 1d Methyl (S)-2-(chloromethyl)-1-(oxetan-2-ylmethyl)-1H-benzo[d]imidazole-6-carboxylate 1c (55 mg, 186.6096 μmol, prepared using the method disclosed in intermediate 23 on page 69 of the specification in patent application WO2018109607) and compound 1b (121 mg, 185.0889 μmol) were dissolved in acetonitrile (10 mL), followed by addition of potassium carbonate (128 mg, 926.1571 μmol), and the reaction solution was stirred at 50° C. for 5 h, cooled to room temperature, and concentrated. The resulting residue was purified by silica gel column chromatography with eluent system A to give the title compound 1d (105 mg, yield: 99%).

MS m/z (ESI): 568.1 [M+1].

Step 3

(S)-2-((6-((4-cyano-2-fluorobenzyl)oxy-3',6'-dihydro-[2,4'-bipyridin]-1'(2'H)-yl)methyl)-1-(oxetan-2-ylmethyl)-1H-benzo[d]imidazole-6-carboxylic acid 1

Compound 1d (105 mg, 184.9865 μmol) was dissolved in a mixed solvent of acetonitrile (5 mL) and water (1 mL), followed by addition of lithium hydroxide (6 mg, 250.5397 μmol), and the reaction solution was stirred at 40° C. overnight, concentrated, adjusted to pH 5-6 with a citric acid solution, dissolved in 2 mL of acetonitrile, and then subjected to high performance liquid chromatography to give 1 (20 mg, yield: 19%).

MS m/z (ESI): 554.2 [M+1].

$^{1}$H NMR (500 MHz, DMSO-$d_6$) δ 8.26 (s, 1H), 7.88 (d, J=9.9 Hz, 1H), 7.81 (d, J=8.3 Hz, 1H), 7.74-7.59 (m, 4H), 7.09 (d, J=7.5 Hz, 1H), 6.77 (d, J=8.1 Hz, 1H), 6.70 (d, J=4.4 Hz, 1H), 5.49 (s, 2H), 5.11-5.01 (m, 1H), 4.79 (dd, J=15.2, 7.3 Hz, 1H), 4.64 (dd, J=15.3, 2.8 Hz, 1H), 4.50-4.43 (m, 1H), 4.41-4.31 (m, 1H), 4.06 (d, J=13.5 Hz, 1H), 3.91 (d, J=13.5 Hz, 1H), 3.30-3.12 (m, 3H), 2.73 (q, J=5.3 Hz, 2H), 2.65 (dd, J=11.1, 7.1 Hz, 1H), 2.48 (s, 1H), 2.39 (t, J=9.5 Hz, 1H).

Example 2

2-((4-(2-(4-chloro-2-fluorophenyl)-2-methylbenzo[d][1,3]dioxol-4-yl)-3,6-dihydropyridin-1(2H)-yl)methyl)-1-(((S)-oxetan-2-yl)methyl)-1H-benzo[d]imidazole-6-carboxylic acid 2

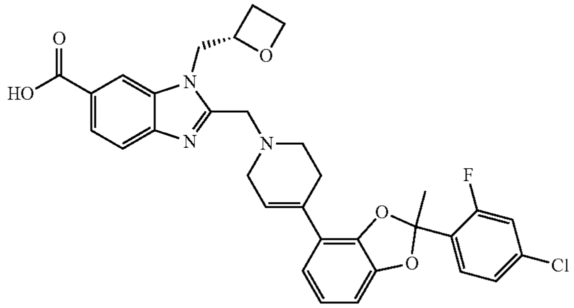

2

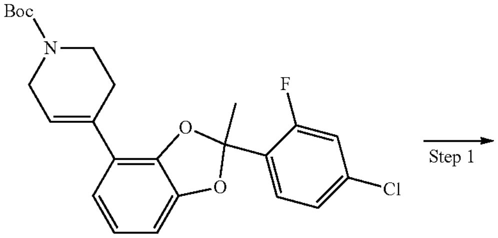

2a

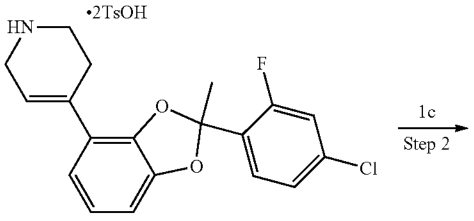

2b

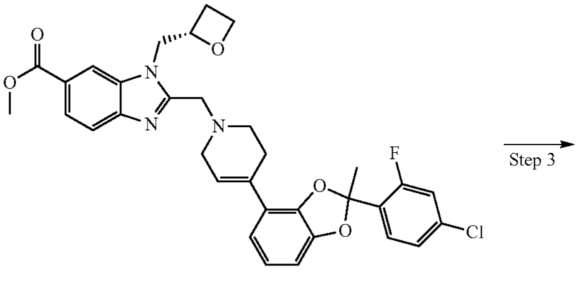

2c

-continued

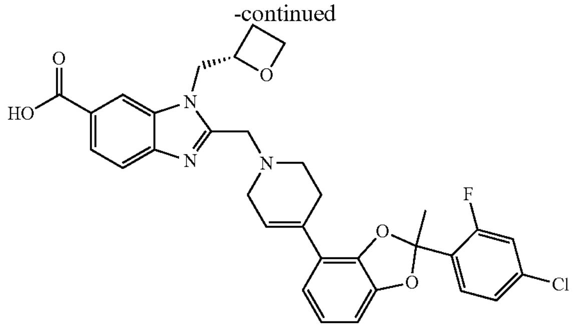

2

Step 1

4-(2-(4-chloro-2-fluorophenyl)-2-methylbenzo[d][1,3]dioxol-4-yl)-1,2,3,6-tetrahydropyridine 2b Tert-Butyl 4-(2-(4-chloro-2-fluorophenyl)-2-methylbenzo[d][1,3]dioxol-4-yl)-5,6-dihydropyridine-1(2H)-carboxylate 2a (65 mg, 0.15 mmol, prepared using the method disclosed in intermediate C5 on page 55 of the specification in patent application WO2019239319) was dissolved in ethyl acetate (5 mL), followed by addition of p-toluenesulfonic acid monohydrate (70 mg, 0.37 mmol), and the reaction solution was stirred at 60° C. for 4 h, cooled, filtered, and washed with ethyl acetate (10 mL). The organic phase was collected, dried, filtered, and concentrated under reduced pressure to give the title compound 2b (75 mg, di-p-toluenesulfonate), which was directly used in the next step without purification.

MS m/z (ESI): 346.1 [M+1].

Step 2

Methyl 2-((4-(2-(4-chloro-2-fluorophenyl)-2-methylbenzo[d][1,3]dioxol-4-yl)-3,6-dihydropyridin-1(2H)-yl)methyl)-1-(((S)-oxetan-2-yl)methyl)-1H-benzo[d]imidazole-6-carboxylate 2c Compound 2b (75 mg, 0.14 mmol, di-p-toluenesulfonate) was dissolved in 10 mL of acetonitrile, followed by addition of compound 1c (40 mg, 0.14 mmol) and potassium carbonate (94 mg, 0.68 mmol), and the reaction solution was heated to 50° C. and stirred for 5 h, cooled to room temperature, and concentrated under reduced pressure. The resulting residue was purified by silica gel column chromatography with eluent system A to give the title compound 2c (35 mg, yield: 42.7%).

MS m/z (ESI): 604.1 [M+1].

Step 3

2-((4-(2-(4-chloro-2-fluorophenyl)-2-methylbenzo[d][1,3]dioxol-4-yl)-3,6-dihydropyridin-1(2H)-yl)methyl)-1-(((S)-oxetan-2-yl)methyl)-1H-benzo[d]imidazole-6-carboxylic acid 2

Compound 2c (35 mg, 0.06 mmol) was dissolved in 5 mL of acetonitrile, followed by addition of lithium hydroxide monohydrate (3 mg, 0.07 mmol) and 1 mL of water at room temperature, and the reaction solution was reacted at 40° C.

for 16 h, cooled to room temperature, and concentrated to remove acetonitrile. The residue was adjusted to pH 6-7 with a citric acid solution, dissolved in acetonitrile, and then subjected to high performance liquid chromatography to give the title compound 2 (20 mg, yield: 58.5%).

MS m/z (ESI): 590.1 [M+1].

$^1$H NMR (500 MHz, DMSO-$d_6$) δ 12.80 (brs, 1H), 8.26 (s, 1H), 7.81 (d, 1H), 7.66 (d, 1H), 7.57-7.54 (m, 2H), 7.33 (d, 1H), 6.87-6.81 (m, 3H), 6.39-6.36 (m, 1H), 5.08-5.04 (m, 1H), 4.82-4.76 (m, 1H), 4.68-4.63 (m, 1H), 4.48-4.43 (m, 1H), 4.39-4.33 (m, 1H), 4.08-4.03 (m, 1H), 3.92-3.88 (m, 1H), 3.29-3.12 (m, 4H), 2.79-2.63 (m, 3H), 2.55-2.36 (m, 4H).

Example 3

2-((6-(1-(4-chloro-2-fluorobenzyl)ethoxy)-3',6'-dihydro-[2,4'-bipyridin]-1'(2'H)-yl)meth yl)-1-((S)-oxetan-2-yl)methyl)-1H-benzo[d]imidazole-6-carboxylic acid 3

3

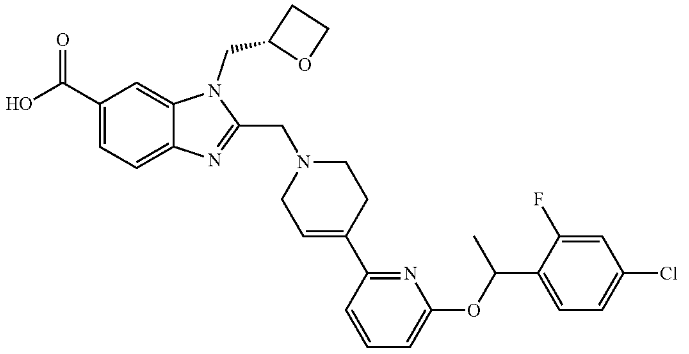

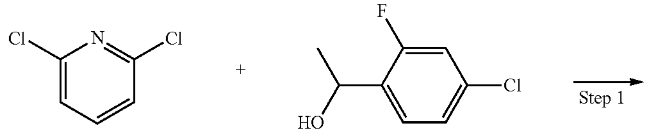

3a 3b

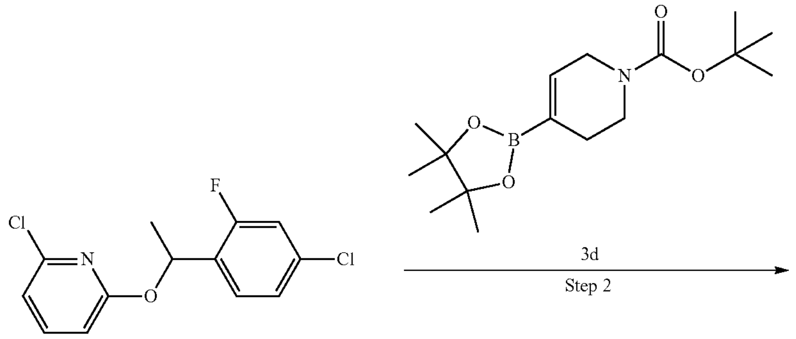

3c

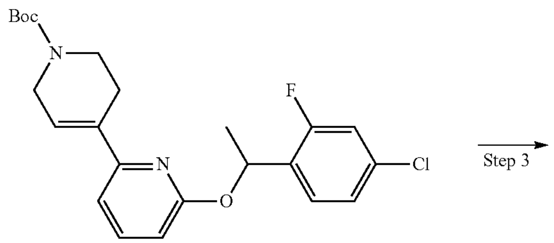

3e

-continued

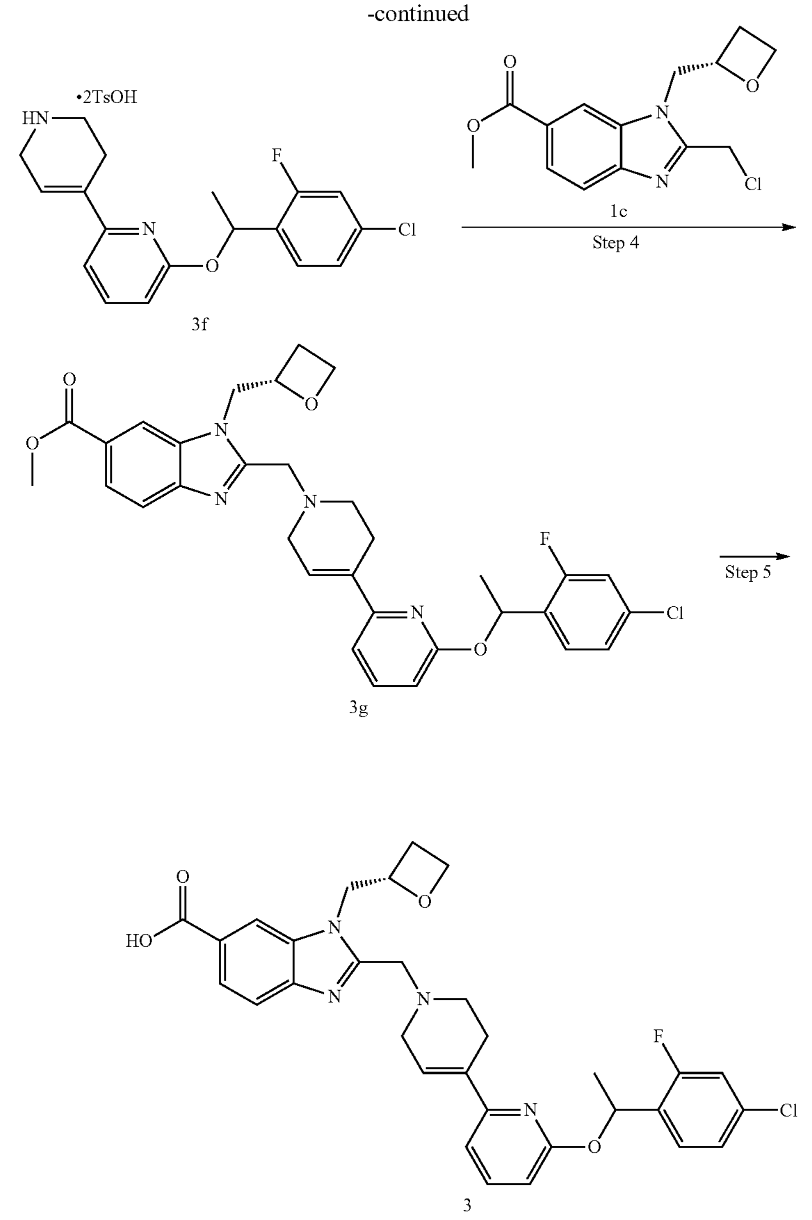

Step 1

2-chloro-6-(1-(4-chloro-2-fluorophenyl)ethoxy)pyridine 3c

Potassium tert-butoxide (672 mg, 5.98 mmol) was added to tetrahydrofuran (10 mL), followed by addition of 1-(4-chloro-2-fluorophenyl)ethanol 3b (523 mg, 2.99 mmol) at room temperature, and the reaction solution was stirred at this temperature for 45 min, added with 2,6-dichloropyridine 3a (444 mg, 3.00 mmol), stirred at room temperature for 1 h, added with water (50 mL), extracted with ethyl acetate (50 mL×3), dried over anhydrous sodium sulfate, filtered, and concentrated. The resulting residue was purified by silica gel column chromatography with eluent system B to give the title compound 3c (700 mg, yield: 81.7%).

Step 2

Tert-Butyl 6-(4-chloro-2-fluorophenyl)ethoxy-3',6'-dihydro-[2,4'-bipyridine]-1'(2'H)-carboxylate 3e Compound 3c (309 mg, 999.32 μmol), anhydrous sodium carbonate (317 mg, 2.99 mmol), tetrakis(triphenylphosphine)palladium(0) (58 mg, 50.19 μmol), water (4 mL) and dioxane (16 mL) were mixed under argon atmosphere, and the reaction solution was stirred at 90° C. overnight. After the reaction was completed as detected by TLC, the resulting residue was purified by silica gel column chromatography with eluent system B to give the title compound 3e (188 mg, yield: 43.5%).

MS m/z (ESI): 433.1 [M+1].

Step 3

6-(1-(4-chloro-2-fluorophenyl)ethoxy)-1'2',3',6'-tetrahydro-2,4'-bipyridine 3f

Compound 3e (188 mg, 434.26 μmol) was dissolved in ethyl acetate (5 mL), followed by addition of p-toluenesulfonic acid (206 mg, 1.08 mmol), and the reaction solution was stirred at 60° C. for 4 h, cooled, filtered, and washed with ethyl acetate (10 mL). The organic phase was collected, dried, filtered, and concentrated under reduced pressure to give the title compound 3f (294 mg, di-p-toluenesulfonate, yield: 99.9%).

MS m/z (ESI): 333.1 [M+1].

Step 4

Methyl 2-((6-((4-chloro-2-fluorophenyl)ethoxy)-3',6'-dihydro-[2,4'-bipyridin]-1'(2'H)-yl)methyl)-1-((S)-oxetan-2-ylmethyl)-1H-benzo[d]imidazole-6-carboxylate 3g Compound 3f (270 mg, 398.69 μmol, 2TsOH) was dissolved in acetonitrile (5 mL), followed by addition of potassium carbonate (135 mg, 976.80 μmol), and the reaction solution was heated to 50° C. and stirred for 5 h, cooled to room temperature, and concentrated under reduced pressure. The resulting residue was purified by silica gel column chromatography with eluent system A to give the title compound 3g (81 mg, yield: 69.6%).

MS m/z (ESI): 591.1 [M+1].

Step 5

2-((6-(1-(4-chloro-2-fluorophenyl)ethoxy)-3',6'-dihydro-[2,4'-bipyridin]-1'(2'H)-yl)meth yl)-1-((S)-oxetan-2-yl)methyl)-1H-benzo[d]imidazole-6-carboxylic acid 3

Compound 3g (80 mg, 135.3475 μmol) was dissolved in acetonitrile (5 mL) and water (1 mL), followed by addition of lithium hydroxide monohydrate (8 mg, 190.47 μmol), and the reaction solution was stirred at 40° C. overnight, concentrated, adjusted to pH 5-6 with citric acid, added with 10 mL of water, extracted with ethyl acetate (30 mL×3), dried over anhydrous sodium sulfate, filtered, and concentrated. The resulting residue was purified by silica gel column chromatography with eluent system A to give the title compound 3 (35 mg, yield: 44.8%).

MS m/z (ESI): 577.1 [M+1].

$^1$H NMR (500 MHz, DMSO-$d_6$) δ 12.75 (s, 1H), 8.26 (d, J=1.6 Hz, 1H), 7.82 (dd, J=8.4, 1.5 Hz, 1H), 7.66 (dd, J=8.1, 3.2 Hz, 1H), 7.45 (td, J=8.2, 2.7 Hz, 1H), 7.41 (dt, J=10.2, 1.6 Hz, 1H), 7.24 (dt, J=8.4, 1.5 Hz, 1H), 7.03 (dd, J=7.5, 2.4 Hz, 1H), 6.72 (d, J=8.1 Hz, 1H), 6.60 (td, J=3.7, 1.9 Hz, 1H), 6.35-6.26 (m, 1H), 5.05 (ddd, J=7.4, 5.0, 2.7 Hz, 1H), 4.79 (dd, J=15.2, 7.3 Hz, 1H), 4.64 (dt, J=15.4, 3.1 Hz, 1H), 4.51-4.42 (m, 1H), 4.36 (ddd, J=6.1, 3.2, 1.8 Hz, 1H), 4.06 (dd, J=13.5, 3.4 Hz, 1H), 3.90 (dd, J=13.5, 5.6 Hz, 1H), 3.27-3.12 (m, 2H), 2.79-2.55 (m, 4H), 2.46 (s, 1H), 2.42-2.29 (m, 2H), 1.57 (d, J=6.6 Hz, 3H).

Example 4

2-((4-((S)-2-(4-chloro-2-fluorophenyl)-2-methylbenzo[d][1,3]dioxol-4-yl)-3,6-dihydropyridin-1(2H)-yl)methyl)-1-(((S)-oxetan-2-yl)methyl)-1H-benzo[d]imidazole-6-carboxylic acid 4

4

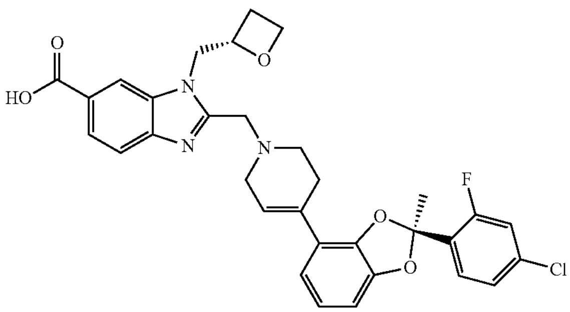

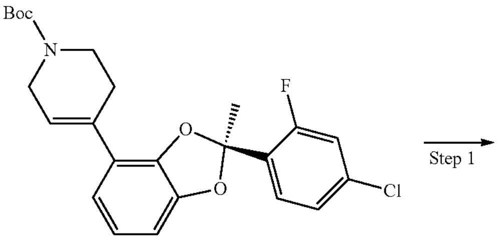

4a

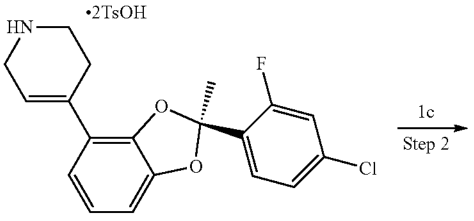

4b

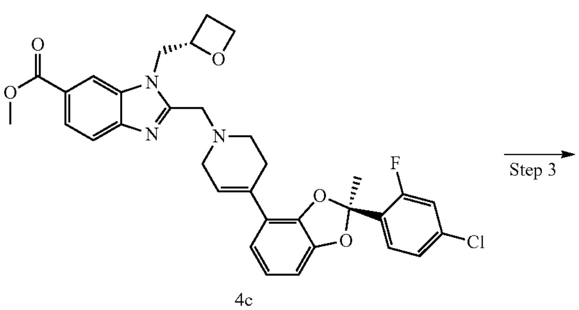

4c

-continued

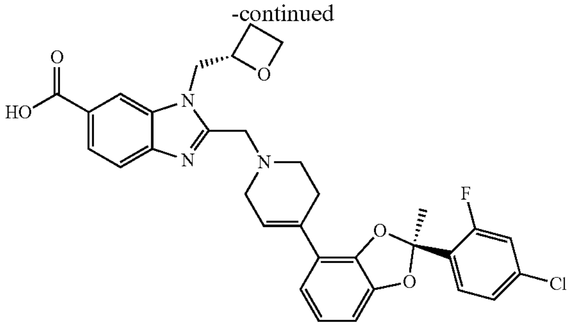

4

Step 1

(S')-4-(2-(4-chloro-2-fluorophenyl)-2-methylbenzo[d][1,3]dioxol-4-yl)-1,2,3,6-tetrahydropyridine-4-methylbenzenesulfonate 4b Tert-Butyl (S)-4-(2-(4-chloro-2-fluorophenyl)-2-methylbenzo[d][1,3]dioxol-4-yl)-1,2,3,6-tetrahydropyridine-1(2H)-carboxylate (4a, 88 mg, 0.20 mmol, prepared using the method disclosed in intermediate C5 of Example on page 55 of the specification in patent application WO2019239319, and through chiral resolution) was dissolved in ethyl acetate (5 mL), followed by addition of p-toluenesulfonic acid monohydrate (94 mg, 0.49 mmol), and the reaction solution was stirred at 60° C. for 4 h, cooled, concentrated under reduced pressure, and washed with n-hexane (20 mL) to give a crude product 4b (102 mg, p-toluenesulfonate), which was directly used in the next reaction without purification.

MS m/z (ESI): 345.9 [M+1].

Step 2

Methyl 2-((4-((S)-2-(4-chloro-2-fluorophenyl)-2-methyl-benzo[d][1,3]dioxol-4-yl)-3,6-dihydropyridin-1(2H)-yl)methyl)-1-(((S)-oxetan-2-yl)methyl)-1H-benzo[d]imidazole-6-carboxylate 4c The crude compound 4b (102 mg, 0.20 mmol, p-toluenesulfonate) was dissolved in 10 mL of acetonitrile, followed by addition of compound 1c (50 mg, 0.17 mmol) and potassium carbonate (117 mg, 0.85 mmol), and the reaction solution was heated to 50° C. and stirred for 5 h, cooled to room temperature, and concentrated under reduced pressure. The resulting residue was purified by silica gel column chromatography with eluent system B to give the title compound 4c (88 mg, yield: 85.9%).

MS m/z (ESI): 604.1 [M+1].

Step 3

2-((4-((S)-2-(4-chloro-2-fluorophenyl)-2-methyl-benzo[d][1,3]dioxol-4-yl)-3,6-dihydropyridin-1(2H)-yl)methyl)-1-(((S)-oxetan-2-yl)methyl)-1H-benzo[d]imidazole-6-carboxylic acid 4

Compound 4c (88 mg, 0.15 mmol) was dissolved in 5 mL of acetonitrile, followed by addition of lithium hydroxide monohydrate (7 mg, 0.17 mmol) and 1 mL of water at room temperature, and the reaction solution was reacted at 40° C. for 16 h, cooled to room temperature, and concentrated under reduced pressure to remove acetonitrile. The residue was adjusted to pH 6-7 with a citric acid solution, dissolved in acetonitrile, and purified by high performance liquid chromatography (Waters-2767, elution system: ammonium bicarbonate, water, and acetonitrile) to give the title compound 4 (50 mg, yield: 58.2%).

MS m/z (ESI): 590.2 [M+1].

$^1$H NMR (500 MHz, DMSO-$d_6$) δ 12.80 (brs, 1H), 8.27 (s, 1H), 7.81 (d, 1H), 7.66 (d, 1H), 7.57-7.54 (m, 2H), 7.33 (d, 1H), 6.87-6.81 (m, 3H), 6.39-6.36 (m, 1H), 5.08-5.04 (m, 1H), 4.82-4.76 (m, 1H), 4.68-4.63 (m, 1H), 4.48-4.43 (m, 1H), 4.39-4.33 (m, 1H), 4.17-4.06 (m, 1H), 4.00-3.90 (m, 1H), 3.32-3.19 (m, 2H), 2.86-2.73 (m, 2H), 2.70-2.64 (m, 1H), 2.60-2.53 (m, 1H), 2.46-2.34 (m, 2H), 2.03 (s, 3H).

Example 5

(S)-2-((6-(4-cyano-2-fluorobenzyl)thio-3',6'-dihydro-[2,4'-bipyridin]-1'(2'H)-yl)methyl)-1-(oxetan-2-ylmethyl)-1H-benzo[d]imidazole-6-carboxylic acid 5

5

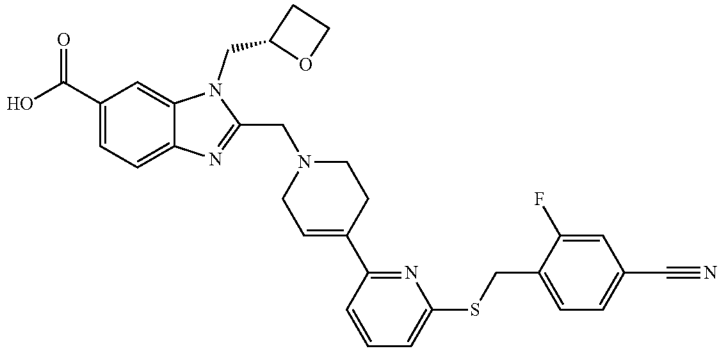

-continued
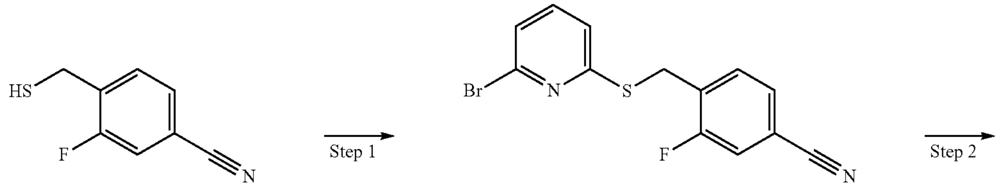
5a 5b
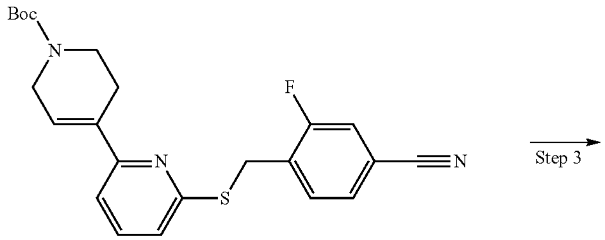
5c
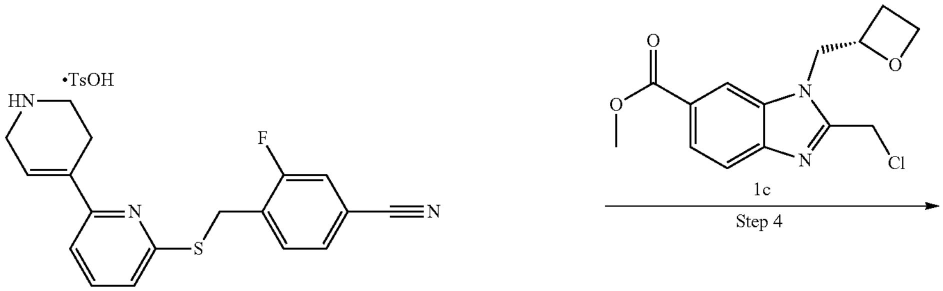
1c
5d
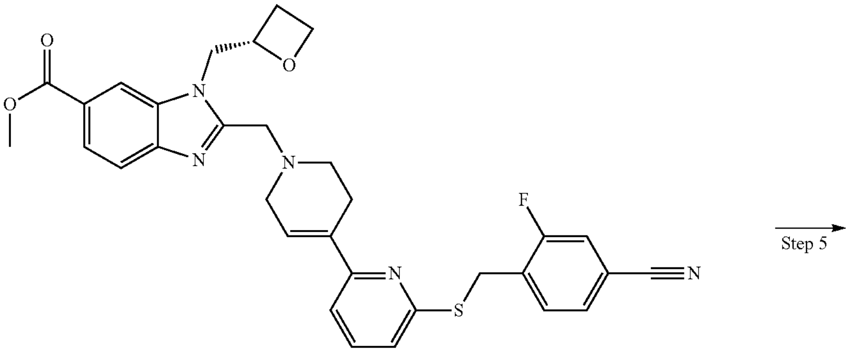
5e
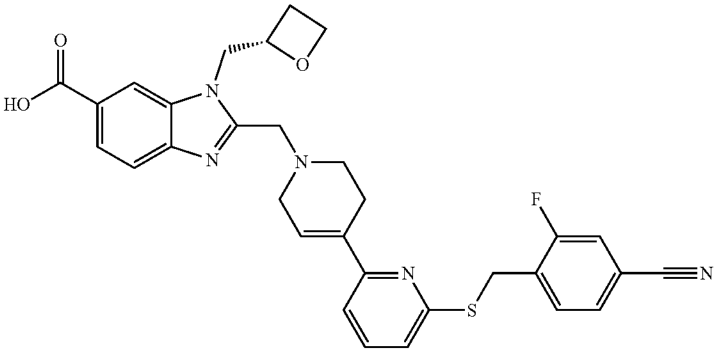
5

Step 1

4-(((6-bromopyridin-2-yl)thio)methyl)-3-fluorobenzonitrile 5b 3-fluoro-4-(mercaptomethyl)benzonitrile 5a (309 mg, 1.84 mmol, prepared using the method disclosed in intermediate I-2 on page 26 of the specification of patent application US2012329788A1) was dissolved in toluene (10 mL), followed by addition of 2,6-dibromopyridine (450 mg, 1.89 mmol, Accela ChemBio Co., Ltd.), 4,5-bisdiphenylphosphine-9,9-dimethylxanthene (100 mg, 0.17 mmol), tris(dibenzylideneacetone)dipalladium(0) (90 mg, 0.10 mmol) and N,N-diisopropylethylamine (600 mg, 4.64 mmol), and the reaction solution was reacted under microwave irradiation at 100° C. for 1 h, cooled to room temperature, and concentrated. The resulting residue was purified by silica gel column chromatography with eluent system B to give the title compound 5b (225 mg, yield: 37.6%).

MS m/z (ESI): 325 [M+1].

Step 2

Tert-Butyl 6-((4-cyano-2-fluorobenzyl)thio)-3',6'-dihydro-[2,4'-bipyridine]-1'(2'H)-carboxylate 5c Compound 5b (255 mg, 0.70 mmol) was dissolved in 1,4-dioxane (10 mL), followed by addition of N-tert-butoxycarbonyl-1,2,5,6-tetrahydropyridine-4-boronic acid pinacol ester (220 mg, 0.71 mmol, Accela ChemBio Co., Ltd.), anhydrous sodium carbonate (220 mg, 2.08 mmol), tetrakis(triphenylphosphine)palladium(0) (40 mg, 0.03 mmol) and water (3 mL), and the reaction solution was heated to 90° C. under nitrogen atmosphere and stirred for 16 h, cooled to room temperature, and concentrated. The resulting residue was purified by silica gel column chromatography with eluent system A to give the title compound 5c (260 mg, yield: 87.8%).

MS m/z (ESI): 426.1 [M+1].

Step 3

3-fluoro-4-(((1',2',3',6'-tetrahydro-[2,4'-bipyridin]-6-yl)thio)methyl)benzonitrile p-toluenesulfonate 5d Compound 5c (125 mg, 0.29 mmol) was dissolved in ethyl acetate (5 mL), followed by addition of p-toluenesulfonic acid monohydrate (170 mg, 0.89 mmol), and the reaction solution was stirred at 60° C. for 4 h, cooled, filtered, and washed with ethyl acetate (10 mL). The organic phase was collected, dried, filtered and concentrated under reduced pressure to give the crude title product 5d (146 mg), which was directly used in the next step without purification.

MS m/z (ESI): 326.1 [M+1].

Step 4

Methyl (S)-2-((6-((4-cyano-2-fluorobenzyl)thio)-3',6'-dihydro-[2,4'-bipyridin]-1'(2'H)-yl)methyl)-1-(oxetan-2-ylmethyl)-1H-benzo[d]imidazole-6-carboxylate 5e Compound 1c (80 mg, 0.27 mmol) and compound 5d (146 mg, 0.29 mmol) were dissolved in acetonitrile (10 mL), followed by addition of potassium carbonate (200 mg, 1.44 mmol), and the reaction solution was stirred at 50° C. for 5 h, cooled to room temperature, and concentrated. The resulting residue was purified by silica gel column chromatography with eluent system B to give the title compound 5e (158 mg, yield: 99%).

MS m/z (ESI): 584.2 [M+1].

Step 5

(S)-2-((6-(4-cyano-2-fluorobenzyl)thio-3',6'-dihydro-[2,4'-bipyridin]-1'(2'H)-yl)methyl)-1-(oxetan-2-ylmethyl)-1H-benzo[d]imidazole-6-carboxylic acid 5

Compound 5e (150 mg, 0.26 mmol) was dissolved in 6 mL of a mixed solvent of acetonitrile and water (V:V=5:1), followed by addition of lithium hydroxide monohydrate (13 mg, 0.31 mmol), and the reaction solution was stirred at 40° C. for 16 h, concentrated, adjusted to pH 5-6 with a citric acid solution, dissolved in acetonitrile (2 mL), and purified by silica gel column chromatography with eluent system A to give the title compound 5 (90 mg, 61.5%).

MS m/z (ESI): 570.1 [M+1].

$^1$H NMR (500 MHz, DMSO-$d_6$) δ 12.71 (brs, 1H), 8.26 (s, 1H), 7.86-7.80 (m, 2H), 7.71-7.59 (m, 4H), 7.25 (d, 1H), 7.17 (d, 1H), 6.72 (s, 1H), 5.08-5.04 (m, 1H), 4.82-4.75 (m, 1H), 4.67-4.63 (m, 1H), 4.54 (s, 2H), 4.49-4.44 (m, 1H), 4.38-4.32 (m, 1H), 4.09-3.91 (m, 2H), 3.28-3.21 (m, 2H), 3.17 (s, 2H), 2.78-2.72 (m, 2H), 2.69-2.62 (m, 1H), 2.43-2.34 (m, 1H).

Example 6
(S)-2-((6-(4-cyano-2-fluorobenzyl)thio-5-fluoro-3',6'-dihydro-[2,4'-bipyridin]-1'(2'H)-yl)methyl)-1-(oxetan-2-ylmethyl)-1H-benzo[d]imidazole-6-carboxylic acid 6
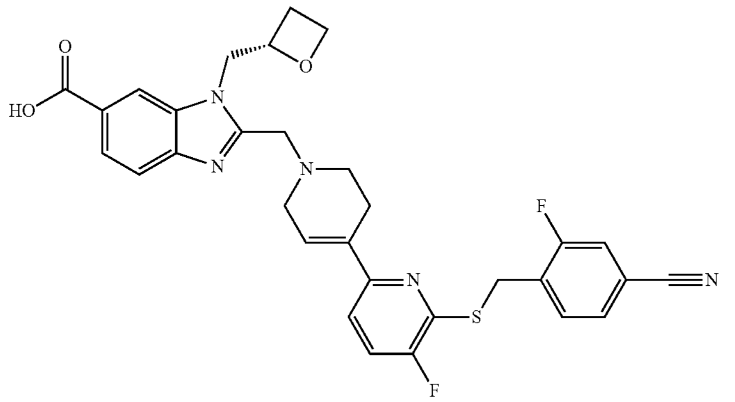
6
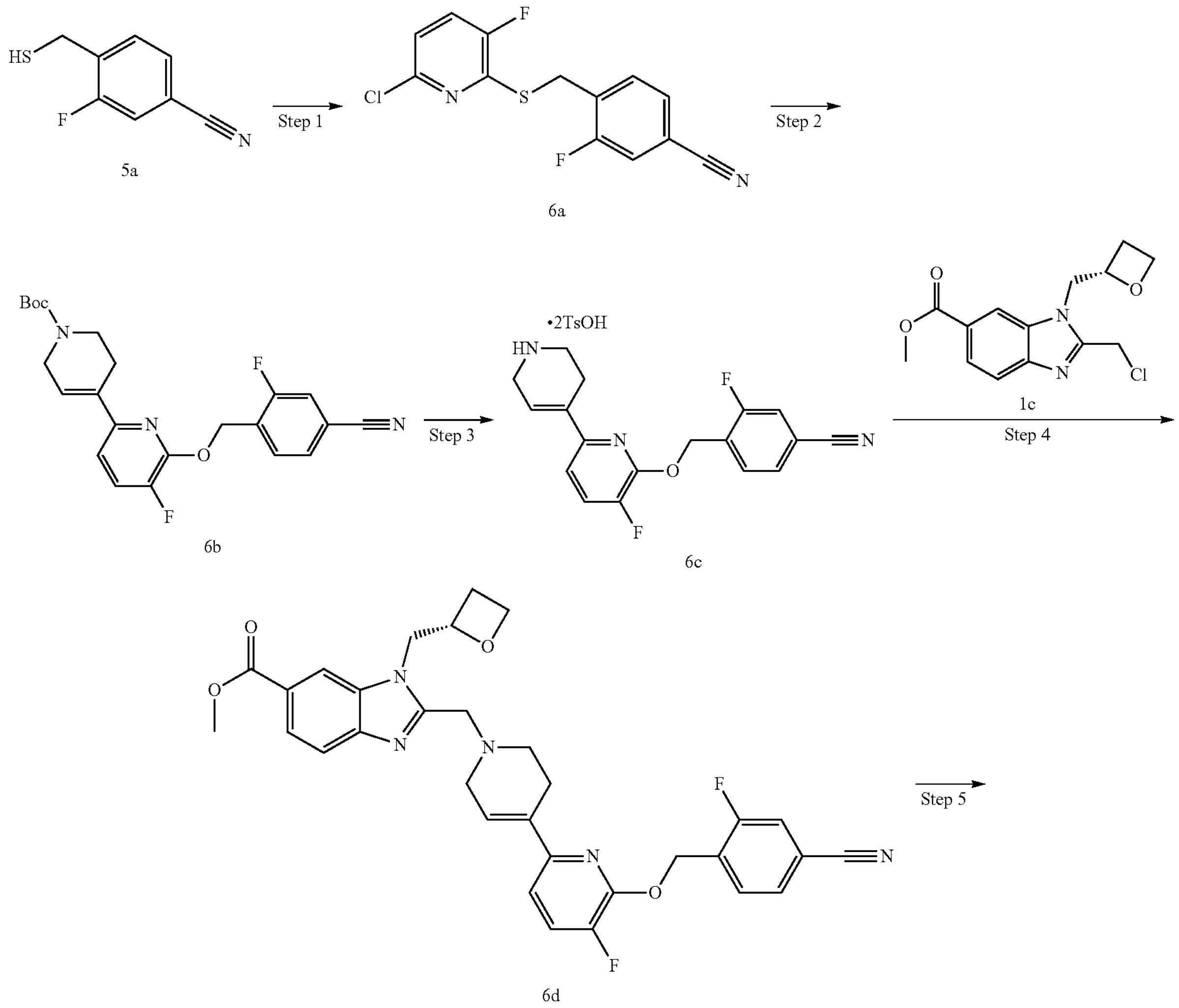

-continued

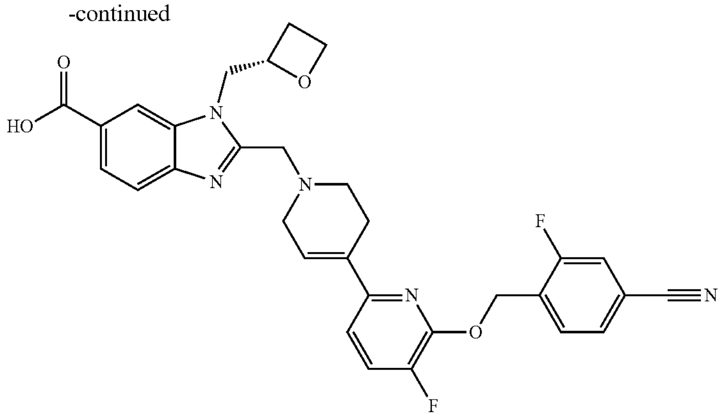

6

Step 1

4-(((6-chloro-3-fluoropyridin-2-yl)thio)methyl)-3-fluorobenzonitrile 6a 3-fluoro-4-(mercaptomethyl)benzonitrile 5a (280 mg, 1.67 mmol) was dissolved in toluene (10 mL), followed by addition of 2,6-dichloro-3-fluoropyridine (280 mg, 1.69 mmol, PharmaBlock Sciences (Nanjing), Inc.), 4,5-bisdiphenylphosphino-9,9-dimethylxanthene (100 mg, 0.17 mmol), tris(dibenzylideneacetone)dipalladium(0) (80 mg, 0.09 mmol) and N,N-diisopropylethylamine (550 mg, 4.26 mmol), and the reaction solution was reacted under microwave irradiation at 100° C. for 1 h, cooled to room temperature, and concentrated. The resulting residue was purified by silica gel column chromatography with eluent system B to give the title compound 6a (128 mg, yield: 25.8%).

MS m/z (ESI): 297.0 [M+1].

Step 2

Tert-Butyl 6-((4-cyano-2-fluorobenzyl)thio)-5-fluoro-3',6'-dihydro-[2,4'-bipyridine]-1'(2'H)-carboxylate 6b Compound 6a (128 mg, 0.43 mmol) was dissolved in 1,4-dioxane (10 mL), followed by addition of N-tert-butoxycarbonyl-1,2,5,6-tetrahydropyridine-4-boronic acid pinacol ester (22.15 g, 0.49 mmol, Accela ChemBio Co., Ltd.), anhydrous sodium carbonate (100 mg, 0.94 mmol), tetrakis (triphenylphosphine)palladium(0) (50 mg, 0.04 mmol) and water (2 mL), and the reaction solution was heated to 90° C. under nitrogen atmosphere and stirred for 4 h, cooled to room temperature, and concentrated. The resulting residue was purified by silica gel column chromatography with eluent system B to give the title compound 6b (126 mg, yield: 65.9%).

MS m/z (ESI): 388.1 [M−55].

Step 3

3-fluoro-4-(((5-fluoro-1',2',3',6'-tetrahydro-[2,4'-bipyridin]-6-yl)thio)methyl)benzonitrile di-p-toluenesulfonate 6c Compound 6b (126 mg, 0.28 mmol) was dissolved in ethyl acetate (5 mL), followed by addition of p-toluenesulfonic acid monohydrate (160 mg, 0.84 mmol), and the reaction solution was stirred at 60° C. for 4 h, cooled, filtered, and washed with ethyl acetate (10 mL). The organic phase was collected, dried, filtered and concentrated under reduced pressure to give the crude title product 6c (195 mg), which was directly used in the next step without purification.

Step 4

Methyl (S)-2-((6-((4-cyano-2-fluorobenzyl)thio)-5-fluoro-3',6'-dihydro-[2,4'-bipyridin]-1'(2'H)-yl)methyl)-1-(oxetan-2-ylmethyl)-1H-benzo[d]imidazole-6-carboxylate 6d Compound 1c (60 mg, 0.20 mmol) and compound 6c (195 mg, 0.28 mmol) were dissolved in acetonitrile (10 mL), followed by addition of potassium carbonate (150 mg, 1.09 mmol), and the reaction solution was stirred at 50° C. for 5 h, cooled to room temperature, and concentrated. The resulting residue was purified by silica gel column chromatography with eluent system B to give the title compound 6d (96 mg, yield: 78.4%).

MS m/z (ESI): 602.1 [M+1].

Step 5

(S)-2-((6-(4-cyano-2-fluorobenzyl)thio-5-fluoro-3',6'-dihydro-[2,4'-bipyridin]-1'(2'H)-yl)methyl)-1-(oxetan-2-ylmethyl)-1H-benzo[d]imidazole-6-carboxylic acid 6

Compound 6d (86 mg, 0.14 mmol) was dissolved in 6 mL of a mixed solvent of acetonitrile and water (V:V=5:1), followed by addition of lithium hydroxide monohydrate (8 mg, 0.19 mmol), and the reaction solution was stirred at 40° C. for 16 h, concentrated, adjusted to pH 5-6 with a citric acid solution, dissolved in acetonitrile (2 mL), and purified by silica gel column chromatography with eluent system A to give the title compound 6 (26 mg, 31.0%).

MS m/z (ESI): 588.2 [M+1].

$^1$H NMR (500 MHz, DMSO-$d_6$) δ 12.77 (brs, 1H), 8.26 (d, 1H), 7.85 (dd, 2H), 7.81 (dd, 1H), 7.67-7.60 (m, 4H), 7.35 (dd, 1H), 6.66 (s, 1H), 5.09-5.04 (m, 1H), 4.82-4.77 (m, 1H), 4.67-4.63 (m, 1H), 4.60 (s, 2H), 4.49-4.44 (m, 1H), 4.38-4.34 (m, 1H), 4.08-3.91 (m, 2H), 3.28-3.17 (m, 2H), 2.78-2.71 (m, 2H), 2.69-2.62 (m, 1H), 2.54-2.51 (m, 1H), 2.43-2.36 (m, 1H).

Example 7

2-((4-((S)-2-(4-chloro-2-fluorophenyl)-2-methyl-benzo[d][1,3]dioxol-4-yl)-3,6-dihydropyridin-1(2H)-yl)methyl)-3-(((S)-oxetan-2-yl)methyl)-3H-imidazo [4,5-b]pyridine-5-carb oxylic acid 7

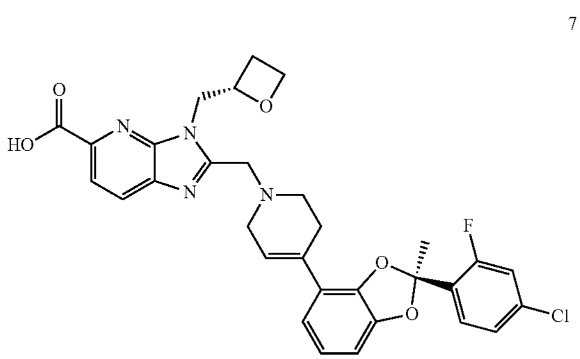

7

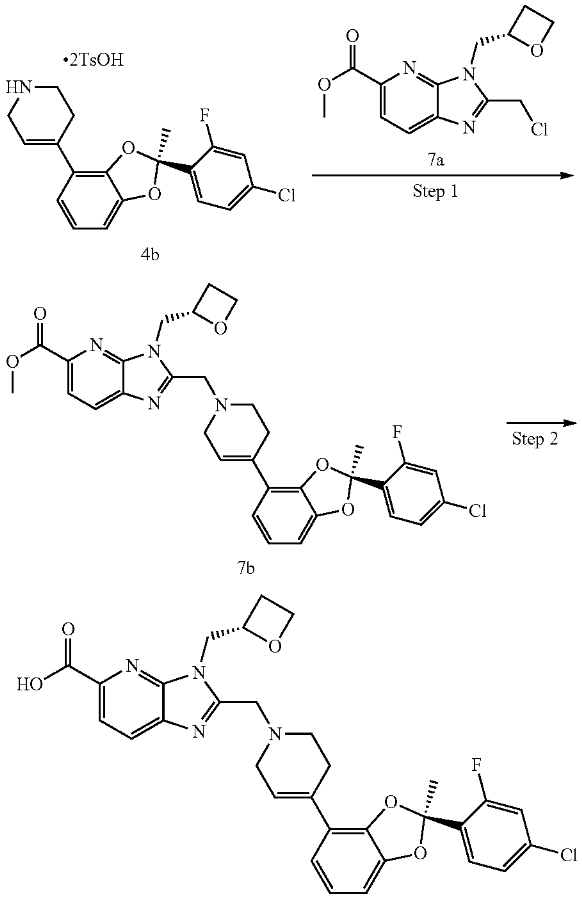

Step 1

Methyl 2-((4-((S)-2-(4-chloro-2-fluorophenyl)-2-methyl-benzo[d][1,3]dioxol-4-yl)-3,6-dihydropyridin-1(2H)-yl)methyl)-3-(((S)-oxetan-2-yl)methyl)-3H-imidazo [4,5-b]pyridine-5-carboxylate 7b The crude compound 4b (83 mg, 0.16 mmol) was dissolved in acetonitrile (5 mL), followed by addition of the compound methyl (S)-2-chloromethyl-3-(oxetan-2-ylmethyl)-3H-imidazo[4,5-b]pyridine-5-carboxylate 7a (45 mg, 0.15 mmol, prepared using the method disclosed in intermediate P27 on page 85 of the specification in the patent application WO2019239371A1) and potassium carbonate (100 mg, 0.72 mmol), and the reaction solution was heated to 50° C. and stirred for 5 h, cooled to room temperature, and concentrated under reduced pressure. The resulting residue was purified by silica gel column chromatography with eluent system B to give the title compound 7b (64 mg, yield: 69.5%).

MS m/z (ESI): 605.1 [M+1].

Step 2

2-((4-((S)-2-(4-chloro-2-fluorophenyl)-2-methyl-benzo[d][1,3]dioxol-4-yl)-3,6-dihydropyridin-1(2H)-yl)methyl)-3-(((S)-oxetan-2-yl)methyl)-3H-imidazo [4,5-b]pyridine-5-carb oxylic acid 7

Compound 7b (64 mg, 0.11 mmol) was dissolved in acetonitrile (5 mL), followed by addition of lithium hydroxide monohydrate (5 mg, 0.12 mmol) and water (1 mL) at room temperature, and the reaction solution was reacted at 40° C. for 16 h, cooled to room temperature, and concentrated under reduced pressure to remove acetonitrile. The residue was adjusted to pH 6-7 with a citric acid solution, dissolved in acetonitrile, and purified by silica gel column chromatography with eluent system A to give the title compound 7 (15 mg, yield: 24.0%).

MS m/z (ESI): 591.0 [M+1].

$^1$H NMR (500 MHz, DMSO-$d_6$) δ8.14 (d, 1H), 8.00 (d, 1H), 7.57-7.53 (m, 2H), 7.34-7.32 (m, 1H), 6.87-6.81 (m, 3H), 6.39-6.36 (m, 1H), 5.18-5.13 (m, 1H), 4.85-4.81 (m, 1H), 4.72-4.68 (m, 1H), 4.49-4.44 (m, 1H), 4.38-4.34 (m, 1H), 4.12 (d, 1H), 4.01 (m, 1H), 3.28-3.23 (m, 2H), 2.81-2.72 (m, 2H), 2.69-2.64 (m, 1H), 2.59-2.54 (m, 1H), 2.48-2.39 (m, 2H), 2.02 (s, 3H).

Biological Evaluation

Test Example 1: Evaluation of Agonist Activity Against GLP-1 Receptor

I. Purpose

This experiment was intended to test the agonist activity of the compound molecules against the GLP-1 receptor and evaluate the in vitro activity of the molecules according to $EC_{50}$. The experiment adopted a ONE-Glo™ Luciferase Assay System (Promega, E6110). Under the action of compound molecules, GLP-1R downstream signaling pathways were activated to cause elevated cAMP level. The combination of cAMP and CRE could start the transcription expression of CRE downstream luciferase genes, the luciferase could emit fluorescence when reacting with substrates thereof, and the activity of the compound for agonizing GLP-1 receptors was reflected by measuring fluorescence signals through a ONE-Glo™ reagent.

II. Method

Stably-expressed CHO-K1/CRE-luc/GLP-1 receptor cell strains (self-construction of GLP-1 receptor plasmid; CRE-luc plasmid Promega E8471) was constructed. CHO-K1/CRE-luc/GLP-1 receptor cells were digested, and resuspended after centrifugation. Single cell suspension was uniformly mixed, and adjusted to a viable cell density of $2.5\times10^5$ cell/mL with a cell culture medium (DME/F-12+10% FBS), and the resulting solution was added to a 96-well cell culture plate at 90 µL/well (Corning, #3903). The plate was incubated in an incubator for 16 h (37° C., 5% $CO_2$).

The compound was dissolved in DMSO to prepare a stock solution with an initial concentration of 20 mM. The starting concentration of the small molecule compound was 0.2 mM, and the compound underwent 3-fold serial dilution for a total of 10 concentration points, with DMSO at the $11^{th}$ point. To another 96-well plate was added 95 µL of cell culture medium (DME/F-12+10% FBS), 5 µL of test samples with different concentrations were added to each well, followed by uniform mixing, and then 10 µL of test samples with different concentrations were added to each well, with two duplicate wells set for each sample. The plate was incubated in an incubator for 6 h (37° C., 5% $CO_2$). The 96-well cell culture plate was taken out, and 100 µL of ONE-Glo™ reagent was added to each well, followed by incubation at room temperature for 10 min. The plate was placed in a microplate reader (EnVision 2105, PE) for determination of chemiluminescence.

III. Data Analysis

Data were processed and analyzed using Microsoft Excel and Graphpad Prism 5. $EC_{50}$ values of the compounds were obtained, and the results are shown in Table 1 below.

TABLE 1

$EC_{50}$ of compounds of the present disclosure for agonist activity against GLP-1 receptor

| Example No. | $EC_{50}$ (nM) | Emax % |
|---|---|---|
| 1 | 0.12 | 110 |
| 2 | 0.92 | 110 |
| 3 | 1.38 | 106 |
| 4 | 0.12 | 104 |
| 5 | 1.93 | 110 |
| 6 | 0.85 | 108 |
| 7 | 0.45 | 107 |

Conclusion: the compounds of the present disclosure have good agonist activity against the GLP-1 receptor.

Test Example 2: Effect of Compounds of the Present Disclosure on hERG Potassium Ion Channel I. Purpose The blocking effect of hERG potassium currents by the compounds of the present disclosure was tested in a stable cell strain transfected with an hERG potassium channel using an automated patch clamp.

II. Method 2.1. Materials and Instruments 2.1.1. Materials:

| Reagent | Supplier | Cat. No. |
|---|---|---|
| FBS | GIBCO | 10099 |
| Sodium pyruvate solution | sigma | S8636-100ML |
| MEM non-essential amino acid solution (100×) | sigma | M7145-100ML |
| G418 sulfate | Enzo | ALX-380-013-G005 |
| MEM | Hyclone | SH30024.01B |
| hERG cDNA | Origene | — |
| pcDNA3.1(+) | invitrogen | V79020 |
| HEK293 human embryonic kidney cells | Cell Bank, Chinese Academy of Sciences | Cat. # GNHu18 |

2.1.2. Instruments:

| Instrument | Supplier | Model |
|---|---|---|
| Patchliner 4 channel | nanion | 2-03-03100-002 |
| Patchliner cleaning station | nanion | 2-02-03201-005 |
| Patchliner cell tank | nanion | 2-02-03105-000 |
| Elektrodenchloridierer Patchliner | nanion | 3-02-03533-000 |
| HEAK EPC10 patch clamp amplifier | nanion | 1-01-10012-000 |
| Osmometer | Gonoter | Gonoter 030 |
| pH meter | Mettle Toledo | FE20 |

2.2. Procedures of Automated Patch Clamp

HEK293 cell lines were transfected with pCDNA3.1(+) from which the hERG gene had been constructed, and then stably-expressed monoclonal HEK293-hERG cell strains were selected by addition of G418. Stably-expressed HEK293-hERG cell strains were subcultured at a density of 1:4 in an MEM/EBSS medium (10% FBS, 400 ag/ml G418, 1% MEM non-essential amino acid solution (100×), 1% sodium pyruvate solution) and subjected to an automated patch clamp experiment within 48-72 h after the start of the culture. On the day of experiment, the cells were digested with 0.2500 pancreatin (life technologies, 12563-029), collected by centrifugation and resuspended in an extracellular fluid (140 mM NaCl, 4 mM KCl, 1 mM $MgCl_2$, 2 mM $CaCl_2$, 5 mMD glucose monohydrate, 10 mM HEPES, pH 7.4, 298 mOsmol) to prepare a cell suspension. The cell suspension was placed on the cell bank of the Patchliner instrument that transferred the cells to the chip (NPC-16) using a negative pressure controller. The negative pressure drew individual cells to the wells of the chip. When a whole-cell model was formed, the instrument generated hERG currents according to the setting of hERG current voltage program, and automatically perfused the compound solutions from low concentrations to high concentrations. The currents at various concentrations of the compound and in the blank control were analyzed by data analysis software provided by HEAK EPC10 patch clamp amplifier (Nanion) and Pathlinersoftware and Pathcontrol HTsoftware.

2.3. Results

The blocking effect of the compounds of the present disclosure on hERG potassium currents was tested through the above assay, and the $IC_{50}$ values obtained are shown in Table 2.

TABLE 2

IC$_{50}$ of compound of the present disclosure for the blocking effect on the hERG potassium ion channel

| Example No. | IC$_{50}$ (μM) |
|---|---|
| 4 | 22 |

Conclusion: the compound of the present disclosure has a weak inhibitory effect on hERG and can reduce side effects caused by the hERG pathway.

The invention claimed is:

1. A compound of formula (I), or a pharmaceutically acceptable salt thereof:

(I)

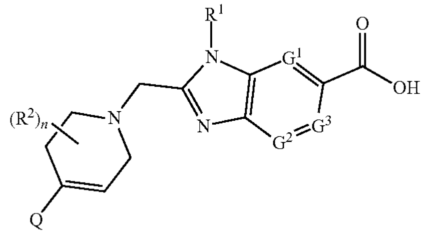

wherein:

Q is Q2;

Q2

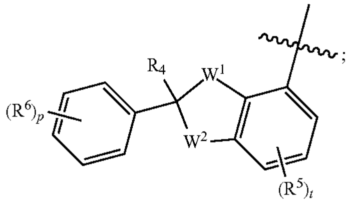

$G^1$, $G^2$ and $G^3$ are each independently $CR^7$ or an N atom;

$W^1$ and $W^2$ are each independently selected from the group consisting of an O atom, an S atom, $NR^{12}$ and $CR^{13}R^{14}$;

$R^1$ is selected from the group consisting of a hydrogen atom, alkyl, alkenyl, alkynyl, haloalkyl, hydroxyalkyl, cycloalkyl, heterocyclyl, aryl and heteroaryl, wherein the alkyl, alkenyl, alkynyl, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

each $R^2$ is independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, alkoxy, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^4$ is selected from the group consisting of a hydrogen atom, halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

each $R^5$ is independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, alkoxy, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

each $R^6$ is independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, alkoxy, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

each $R^7$ is independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

each $R^{12}$ is independently selected from the group consisting of a hydrogen atom, alkyl, alkenyl, alkynyl, haloalkyl, hydroxyalkyl, amino, hydroxy, cycloalkyl, heterocyclyl, aryl and heteroaryl;

each $R^{13}$ and $R^{14}$ is independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

n is 0, 1, 2, 3, 4 or 5;

t is 0, 1, 2 or 3; and p is 0, 1, 2, 3, 4 or 5.

2. The compound or the pharmaceutically acceptable salt thereof according to claim 1, wherein $G^1$ is CH or an N atom; and $G^2$ and $G^3$ are both CH.

3. The compound or the pharmaceutically acceptable salt thereof according to claim 1, being a compound of formula (II), or a pharmaceutically acceptable salt thereof:

(II)

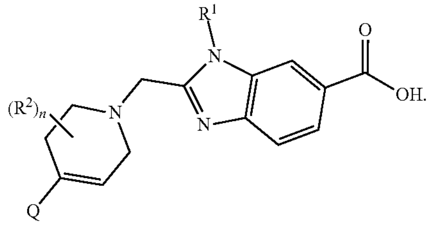

4. The compound or the pharmaceutically acceptable salt thereof according to claim 1, wherein Q is Q4:

Q4

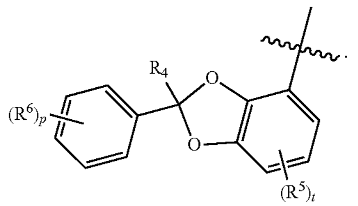

5. The compound or the pharmaceutically acceptable salt thereof according to claim 1, being a compound of formula (III), or a pharmaceutically acceptable salt thereof:

(III)

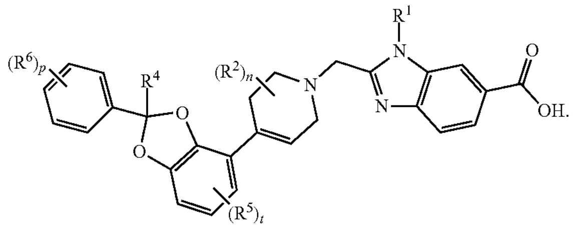

6. The compound or the pharmaceutically acceptable salt thereof according to claim 1, being a compound of formula (IIIaa), or a pharmaceutically acceptable salt thereof:

(IIIaa)

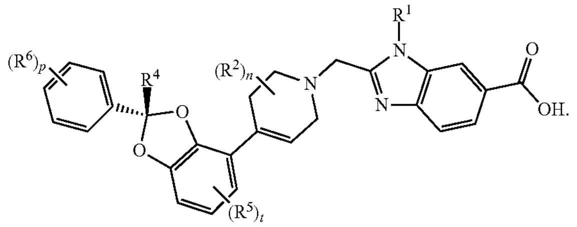

7. The compound or the pharmaceutically acceptable salt thereof according to claim 1, wherein $R^1$ is $C_{1-6}$ alkyl, wherein the $C_{1-6}$ alkyl is optionally substituted with one or more substituents selected from the group consisting of halogen, hydroxy, $C_{1-6}$ alkoxy, 3- to 6-membered cycloalkyl and 3- to 6-membered heterocyclyl.

8. The compound or the pharmaceutically acceptable salt thereof according to claim 1, wherein each $R^2$ is independently a hydrogen atom or $C_{1-6}$ alkyl.

9. The compound or the pharmaceutically acceptable salt thereof according to claim 1, wherein $R^4$ is a hydrogen atom or $C_{1-6}$ alkyl.

10. The compound or the pharmaceutically acceptable salt thereof according to claim 1, wherein each $R^5$ is independently selected from the group consisting of a hydrogen atom, halogen and $C_{1-6}$ alkyl.

11. The compound or the pharmaceutically acceptable salt thereof according to claim 1, selected from the group consisting of:

2

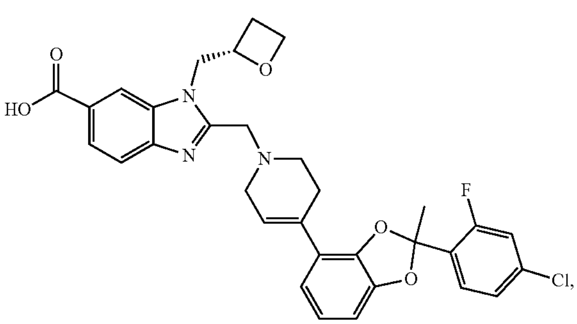

4

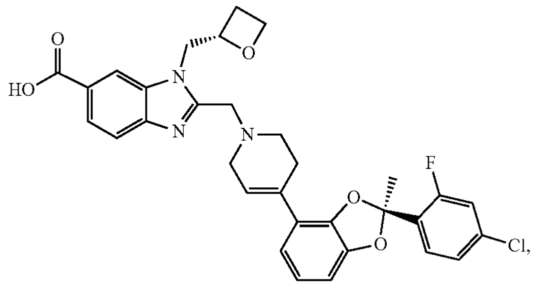

and

7

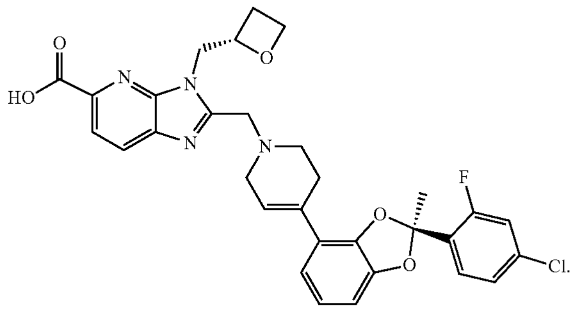

12. A compound of formula (IA) or a pharmaceutically acceptable salt thereof, (IA)

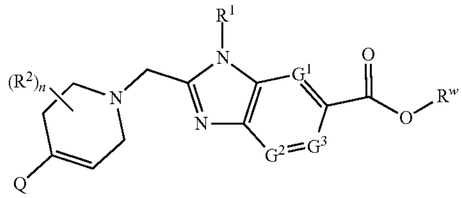

wherein:

$R^w$ is $C_{1-6}$ alkyl;

Q is Q2:

Q2

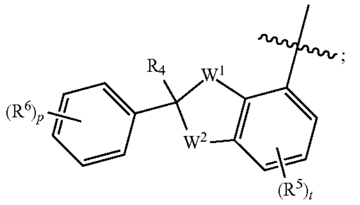

$G^1$, $G^2$ and $G^3$ are each independently $CR^7$ or an N atom;

$W^1$ and $W^2$ are each independently selected from the group consisting of an O atom, an S atom, $NR^{12}$ and $CR^{13}R^{14}$, $R^1$ is selected from the group consisting of a hydrogen atom, alkyl, alkenyl, alkynyl, haloalkyl, hydroxyalkyl, cycloalkyl, heterocyclyl, aryl and heteroaryl, wherein the alkyl, alkenyl, alkynyl, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

each $R^2$ is independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, alkoxy, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^4$ is selected from the group consisting of a hydrogen atom, halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

each $R^5$ is independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, alkoxy, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

each $R^6$ is independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl, wherein the alkyl, alkenyl, alkynyl, alkoxy, cycloalkyl, heterocyclyl, aryl and heteroaryl are optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

each $R^7$ is independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

each $R^{12}$ is independently selected from the group consisting of a hydrogen atom, alkyl, alkenyl, alkynyl, haloalkyl, hydroxyalkyl, amino, hydroxy, cycloalkyl, heterocyclyl, aryl and heteroaryl;

each $R^{13}$ and $R^{14}$ is independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

n is 0, 1, 2, 3, 4 or 5;

t is 0, 1, 2 or 3; and p is 0, 1, 2, 3, 4 or 5.

13. A compound, or a pharmaceutically acceptable salt thereof, selected from the group consisting of:

2c

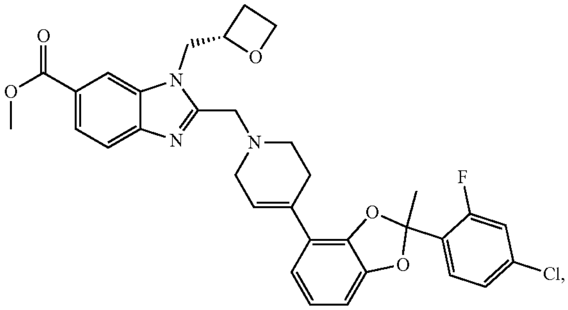

,

4c

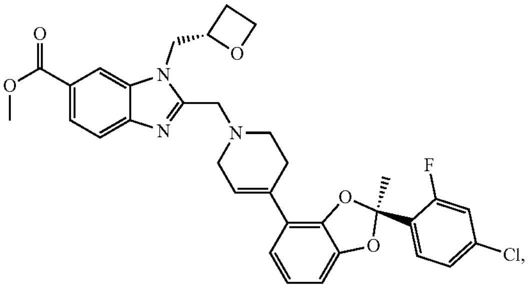

, and

7b

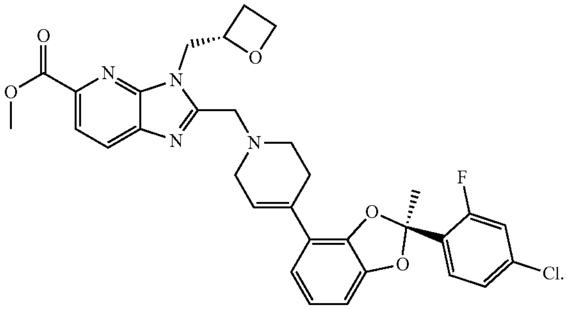

.

14. A method for preparing the compound or the pharmaceutically acceptable salt thereof according to claim 1, comprising:

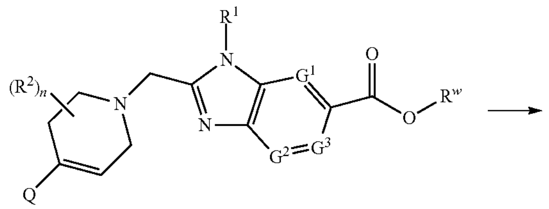

(IA)

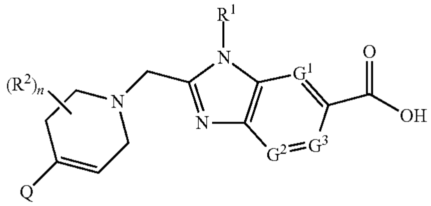

(I)

subjecting a compound of formula (IA) to a hydrolysis reaction to obtain the compound of formula (I), wherein:

$R^w$ is $C_{1-6}$ alkyl.

15. A pharmaceutical composition, comprising the compound or the pharmaceutically acceptable salt thereof according to claim 1, and one or more pharmaceutically acceptable carriers, diluents or excipients.

16. A method for treating a disease, disorder, or condition selected from type II diabetes, maturity-onset diabetes of the young (MODY), malnutrition-related diabetes, gestational diabetes, diabetic complications, obesity, insulin resistance and hepatic insulin resistance, comprising administering to a patient in need thereof the compound of claim 1, or a pharmaceutically acceptable salt thereof.

17. The compound or the pharmaceutically acceptable salt thereof according to claim 1, wherein $R^4$ is $C_{1-6}$ alkyl.

18. The compound or the pharmaceutically acceptable salt thereof according to claim 1, wherein each $R^6$ is independently selected from the group consisting of a hydrogen atom, halogen and $C_{1-6}$ alkyl.

19. The method according to claim 16, wherein the disease, disorder, or condition is type II diabetes, obesity, or diabetic complications.

20. The method according to claim 16, wherein the disease, disorder, or condition is obesity.

21. The method according to claim 16, wherein the disease, disorder, or condition is type II diabetes.

* * * * *